(12) United States Patent
Koenig et al.

(10) Patent No.: US 9,461,120 B2
(45) Date of Patent: Oct. 4, 2016

(54) ELECTRONIC DEVICE

(71) Applicant: Infineon Technologies AG, Neubiberg (DE)

(72) Inventors: Matthias Koenig, Regensburg (DE); Guenther Ruhl, Regensburg (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 0 days.

(21) Appl. No.: 14/633,159

(22) Filed: Feb. 27, 2015

(65) Prior Publication Data

US 2016/0254355 A1    Sep. 1, 2016

(51) Int. Cl.
*H01L 29/16* (2006.01)
*H01L 29/66* (2006.01)

(52) U.S. Cl.
CPC ..... *H01L 29/1606* (2013.01); *H01L 29/66977* (2013.01)

(58) Field of Classification Search
None
See application file for complete search history.

(56) References Cited

U.S. PATENT DOCUMENTS

2013/0248823 A1* 9/2013 Bol ............... H01L 21/02527
257/29
2014/0306184 A1  10/2014 Ruhl et al.

OTHER PUBLICATIONS

Robinson et al. "Contacting graphene." Applied Physics Letters 98.5 (2011): 053103, 2011, 3 pages.
Leong et al. "Low-Contact-Resistance Graphene Devices with Nickel-Etched-Graphene Contacts." ACS nano 8.1, 2013, 994-1001.
Wang et al. American Association for the Advancement of Science, „One-Dimensional Electrical Contact to a Two-Dimensional Material Science 342, 614, 2013, 5 pages.
Van Zeghbroeck, „Principles of Semiconductor Devices, http://ece-www.colorado.edu/~bart/book/, Feb. 2002, 515 pages.

(Continued)

*Primary Examiner* — Joseph Schoenholtz
(74) *Attorney, Agent, or Firm* — Viering, Jentschura & Partner mbB

(57) ABSTRACT

According to various embodiments, an electronic device may include: a layer including a two-dimensional material; a dielectric structure at a first side of the layer, wherein the dielectric structure includes a first contact region and a second contact region, the first contact region defining a first contact area of the layer and the second contact region defining a second contact area of the layer, and the first contact region and the second contact region further defining a device area of the layer between the first contact area and the second contact area of the layer; a first electrode and a second electrode disposed at a second side of the layer opposite to the first side, wherein the first electrode is in direct physical contact with the first contact area of the layer and wherein the second electrode is in direct physical contact with the second contact area of the layer, wherein the first contact region and the second contact region of the dielectric structure are configured to adjust an electric characteristic of the two-dimensional material in the first contact area and in the second contact area of the layer, respectively, so that the electric characteristic of the two-dimensional material in the first contact area and in the second contact area of the layer is different from the electric characteristic of the two-dimensional material in the device area of the layer.

18 Claims, 8 Drawing Sheets

(56) References Cited

OTHER PUBLICATIONS

Nagashio et al., "Metal/Graphene Contact as a Performance Killer of Ultra-high Mobility Graphene—Analysis of Intrinsic Mobility and Contact Resistance-", 2009, 4 pages, IEEE.

Smith et al., "Reducing Contact Resistance in Graphene Devices through Contact Area Patterning", 2013, 3661-3667, ASC-Nano vol. 7 No. 4.

Fengnian Xia et al. "The origins and limits of metal—graphene junction resistance" Nature Nanotechnology, Feb. 6, 2011, 6 pages, Macmillion Publishers Limited.

* cited by examiner

ELECTRONIC DEVICE

TECHNICAL FIELD

Various embodiments relate generally to an electronic device.

BACKGROUND

In general, forming a very thin layer of a material, e.g. with a thickness in the nanometer range or with a thickness even smaller than one nanometer, may be very challenging using typical processes of semiconductor industry. However, so-called two dimensional materials may be highly attractive for electronic devices and integrated circuit technologies. Graphene for example, including a layer of carbon atoms in a hexagonal arrangement, may have superior electronic properties enabling, for example, the manufacturing of a transistor having an increased response and/or switching behavior. Further, an ultrathin layer of a material may have enhanced properties compared to the corresponding bulk material. Therefore, two-dimensional materials could be important for microelectronics, e.g. for developing various types of sensors, transistors, and the like, wherein the challenging task may be incorporating these two-dimensional materials into a microchip for emulating the common silicon technology.

SUMMARY

According to various embodiments, an electronic device may include: a layer including a two-dimensional material; a dielectric structure at a first side of the layer, wherein the dielectric structure includes a first contact region and a second contact region, the first contact region defining a first contact area of the layer and the second contact region defining a second contact area of the layer, and the first contact region and the second contact region further defining a device area of the layer between the first contact area and the second contact area of the layer; a first electrode and a second electrode disposed at a second side of the layer opposite to the first side, wherein the first electrode is in direct physical contact with the first contact area of the layer and wherein the second electrode is in direct physical contact with the second contact area of the layer, wherein the first contact region and the second contact region of the dielectric structure are configured to adjust an electric characteristic of the two-dimensional material in the first contact area and in the second contact area of the layer, respectively, so that the electric characteristic of the two-dimensional material in the first contact area and in the second contact area of the layer is different from the electric characteristic of the two-dimensional material in the device area of the layer.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

Figure 1A:
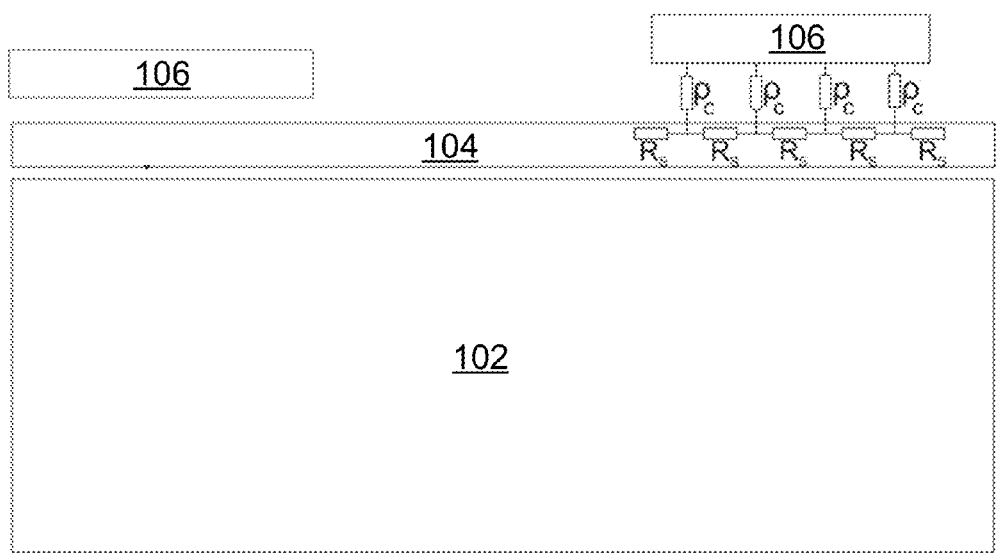
FIG. 1A schematically illustrates an equivalent circuit of an electrically contacted layer including a two-dimensional material.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

The term "lateral" used with regards to the "lateral" extension of a structure (or of a structure element) provided at least one of on or in a carrier (e.g. a substrate, a wafer, or a semiconductor work piece) or "laterally" next to, may be used herein to mean an extension or a positional relationship along a surface of the carrier. That means that a surface of a carrier (e.g. a surface of a substrate, a surface of a wafer, or a surface of a semiconductor work piece) may serve as reference, commonly referred to as the main processing surface. Further, the term "width" used with regards to a "width" of a structure (or of a structure element) may be used herein to mean the lateral extension of a structure. Further, the term "height" used with regards to a height of a structure (or of a structure element), may be used herein to mean an extension of a structure along a direction perpendicular to the surface of a carrier (e.g. perpendicular to the main processing surface of a carrier). The term "thickness" used with regards to a "thickness" of a layer may be used herein to mean the spatial extension of the layer perpendicular to the surface of the support (the material or material structure) on which the layer is deposited. If a surface of the support is parallel to the surface of the carrier (e.g. parallel to the main processing surface) the "thickness" of the layer deposited on the surface of the support may be the same as the height of the layer. Further, a "vertical" structure may be referred to as a structure extending in a direction perpendicular to the lateral direction (e.g. perpendicular to the main processing surface of a carrier) and a "vertical" extension may be referred to as an extension along a direction perpendicular to the lateral direction (e.g. an extension perpendicular to the main processing surface of a carrier).

According to various embodiments, a carrier (e.g. a substrate, a wafer, or a work piece) may be made of or may include semiconductor materials of various types, including, for example, silicon, germanium, Group III to V or other types, including polymers, for example, although in another embodiment, other suitable materials can also be used. In an embodiment, the carrier is made of silicon (doped or undoped), in an alternative embodiment, the carrier is a silicon on insulator (SOI) wafer. As an alternative, any other suitable semiconductor materials can be used for the carrier, for example semiconductor compound material such as gallium arsenide (GaAs), indium phosphide (InP), but also any suitable ternary semiconductor compound material or quaternary semiconductor compound material such as indium gallium arsenide (InGaAs). According to various embodiments, the carrier may be a thin or an ultrathin substrate or wafer, e.g. with a thickness in the range from about several micrometers to about several tens of micrometers, e.g. in the range from about 5 μm to about 50 μm, e.g. with a thickness less than about 100 μm or less than about 50 μm. Further, the carrier may be a silicon wafer with a thickness of about 750 μm. According to various embodiments, a carrier may include SiC (silicon carbide) or may be a silicon carbide carrier, a silicon carbide substrate, a silicon carbide wafer, or a silicon carbide work piece. According to various embodiments, a carrier may include $SiO_2$ (silicon oxide) or may be a silicon oxide carrier, a silicon oxide substrate, a silicon oxide wafer, or a silicon oxide work piece. Further, a carrier may include an electrically isolating material (in other words a dielectric material or an electrically insulating material) at a surface of the carrier or the carrier may consist of an electrically isolating material so that an electrically conductive layer, e.g. a graphene layer, may be formed and functionalized at the surface of the carrier.

In general, the physical and chemical properties of a material may not be defined exclusively by its crystal structure and chemical composition. Since the physical properties, for example the electronic properties (e.g. the band structure), of a surface of a material may differ from the physical properties of the bulk material, there may be a difference regarding the physical properties of a layer or region, if at least one spatial extension of the layer or region is reduced to the nanometer range or even sub-nanometer range. In this case, the surface properties of the respective material forming the layer or region may dominate the characteristics (e.g. physical and chemical properties) of the layer or the region. In the limiting case, at least one dimension of a layer or region may have a spatial extension of several angstroms, which may be the spatial extension of exactly one monolayer of atoms of the respective material.

A monolayer may be a layer having a lateral extension and a layer thickness (or height) perpendicular to the lateral extension, the layer including a plurality of atoms (or molecules), wherein the layer has a thickness (or height) of one single atom (or molecule). In other words, a monolayer of a material may not have equal atoms (or molecules) being arranged above each other (along the thickness or height direction).

According to various embodiments, there may be several different materials intrinsically forming monolayers, so-called self-assembled monolayers, which may be referred to as two-dimensional materials, or more precisely as structural two-dimensional materials. Further, a typical representative of such a structural two-dimensional material may be graphene, consisting of a hexagonal two-dimensional arrangement of carbon atoms, a so-called honey-comb structure. According to various embodiments, graphene may be also referred to as a graphene sheet or a graphene layer. A further representative of a structural two-dimensional material may be hydrogenated graphene (graphane), or partially hydrogenated graphene. In pure graphene sheets, the structural arrangement and the bindings of the carbon atoms may be described using hybridization (hybrid atomic orbitals), wherein in this case the carbon atoms are $sp^2$-hybrids, which means that a covalent bonding of the carbon atoms forms a hexagonal two-dimensional layer, i.e. a hexagonal monolayer. In hydrogenated graphene or graphane, the carbon atoms may be $sp^3$-hybrids or a mixture of $sp^2$-hybrids and $sp^3$-hybrids, wherein the carbon atoms being $sp^3$-hybrids are connected to a hydrogen atom, forming a sheet like (two-dimensional) structure.

A two-dimensional material, as referred to herein, may be a layer having covalent bonding along two spatial directions forming a sheet structure or a two-dimensional structure, e.g. self-assembled, wherein the two-dimensional material may not have a covalent bonding to other atoms outside the sheet structure. A two-dimensional material, as referred to herein, may be a layer consisting of a monolayer of a material. A two-dimensional material, as referred to herein, may be a layer consisting of a bilayer of a material. According to various embodiments, a graphene layer may include carbon in a two-dimensional structure, e.g. in a hexagonally arranged lattice.

Typical three-dimensional materials, e.g. metal bulk material, may have different physical and chemical properties, depending on the lateral extension of the material, e.g. a monolayer or an ultra-thin layer of a material may have different properties than a bulk of the same material. A monolayer or an ultra-thin layer of a three-dimensional material may have different properties than a thicker layer of the material, since the volume to surface ratio is changing. Therefore the properties of a thin layer of a material may approach the bulk properties of the material with increasing layer thickness.

In contrast, a layer including a structural two-dimensional material, e.g. graphene, graphane, silicene, germanene, may retain its physical and chemical properties independently from the layer thickness, e.g. a monolayer of a structural two-dimensional material may have substantially the same properties as a plurality of monolayers arranged above each other, since the individual layers may not be substantially coupled to each other, e.g. since there may be no covalent, ionic, and/or metallic bonding between the individual layers of a structural two-dimensional material. According to various embodiments, a plurality of graphene layers or sheets stacked above each other may be weakly coupled with each other (e.g. via van der Waals interaction).

A conformal layer, as described herein, may exhibit only small thickness variations along the interface with another body, e.g. the layer may exhibit only small thickness variations along edges, steps or other elements of the morphology of the interface. A monolayer of a material covering a surface of an underlying body or base structure (e.g. in direct contact) may be regarded as a conformal layer. A monolayer or a bilayer of a structural two-dimensional material covering a surface of an underlying body or base structure (e.g. in direct contact) may be regarded as a conformal layer. According to various embodiments, depositing conformal layers may enable to form an electronic device, as described herein, in any three-dimensional structure using commonly available deposition techniques and patterning techniques.

As described herein, a structural two-dimensional material may exhibit unique physical and/or chemical properties. Graphene, for example, may be a semiconductor (e.g. a zero-gap semiconductor if no electrical field is applied vertically to the graphene sheet), or a semi-metal having a very high charge carrier mobility (e.g. in the range from about 50,000 to about 200,000 $cm^2/Vs$ on an electrically insulating substrate). Further, graphene may have other unique properties (electrical, mechanical, magnetic, thermal, optical, and the like), making graphene interesting for electronic industry (e.g. for the use in sensors (gas sensors, magnetic sensors), as electrodes, in transistors, as quantum dots, and the like). However, using graphene, as well as other promising structural two-dimensional materials, may include one or more graphene layers (e.g. a graphene monolayer, e.g. a graphene bilayer, e.g. a graphene multilayer) disposed on an electrically insulating substrate, e.g. on silicon dioxide.

Manufacturing methods typically used for providing graphene, e.g. on an electrically insulating substrate (also referred to as dielectric substrate or dielectric layer), may include segregation of carbon from a metal. Illustratively, one or more graphene sheets may be formed directly on a surface of a carrier of a layer. Alternatively, one or more graphene sheets already grown on an auxiliary carrier may be transferred to a carrier or to a layer.

As described before, graphene disposed on an electrically insulating substrate may have, for example, a very high charge carrier mobility. But it was recognized that the electrical contact between metals (or any other material used as electrodes) and graphene has a very high impedance. This is for any electronic components a major obstacle, since thereby, for example, the switching frequency, the energy efficiency, the maximum switchable power, the sensitivity and/or the long-term stability of switching components and/or sensor components may be greatly reduced.

Various embodiments relate to an electronic device including a layer of a two-dimensional material which is electrically contacted by at least one electrode, wherein the contact resistance between the two-dimensional material and the at least one electrode is adjusted, e.g. minimized. Various embodiments are based on the finding, that the electrical contact resistance of a metal-graphene contact (or, in general, the electrical contact resistance of a contact between an electrically conductive material and a two-dimensional material) may be adjusted (e.g. raised or lowered) by subjecting the metal-graphene contact to a strong electrical field, e.g. with an electric field strength greater than about 1 MV/m, e.g. in the range from about 0.5 MV/m to about 2 MV/m, or greater than about 2 MV/m.

Using commonly applied techniques for electrically contacting a graphene layer may cause a high contact resistance, and therefore, a commonly used metal-graphene contact may be not sufficient for an efficient use of graphene in electronics. There may be complex methods for patterning the graphene layer in a region below the electrode that is electrically contacting the graphene layer; however this may only lead to a small reduction of the contact resistance. Further, one-dimensional graphene may be laterally contacted; however, this may require a very complex construction.

According to various embodiments, a charge accumulation may be provided or generated within a dielectric material so that the charge accumulation is located below or above an electrode that electrically contacts a two-dimensional material layer, wherein the two-dimensional material layer is, for example, disposed between the charge accumulation and the electrode. The charge accumulation is electrically separated (in other words electrically isolated) from the electrode and from the two-dimensional material. Illustratively, the electrical field generated by the charge accumulation may influence the contact resistance between the electrode and the two-dimensional material. An electrode for electrically contacting the two-dimensional material may include a metal, a metal alloy, an electrically conductive oxide, a doped semiconductor material or any other electrically conductive material.

According to various embodiments, the charge accumulation provided or generated in the vicinity of a metal/graphene contact may reduce the sheet resistance of the graphene, and therefore, the whole contact resistance may be reduced.

FIG. 1A illustrates a layer 104 including a two-dimensional material, wherein the layer 104 is formed over a dielectric carrier 102 or over a dielectric layer 102, and wherein the layer 104 is electrically contacted by two electrodes 106. FIG. 1A is a schematic view including an equivalent circuit for the contact resistance between the layer 104 and one of the electrodes 106 electrically contacting the layer 104, wherein, for reasons of clarity, the carrier 102, the layer 104, and the electrodes 106 are depicted having respectively a gap between each other, which is not the case for a working device.

As illustrated for example in FIG. 1A, the contact resistance (e.g. if the layer 104 includes graphene and the electrode 106 includes a metal, the contact resistance of a metal/graphene contact) may be composed of a first component, the sheet-resistance ($R_S$) of the layer 104, and a second component, the transition resistance ($\rho_c$) between the layer 104 (e.g. graphene) and the electrode 106 (e.g. the metal). Illustratively, the contact resistance can be understood as a resistor network.

The contact resistance generally results, for example, first from the layer 104 that shall be electrically contacted and second from the transition from the layer 104 to the electrode 106 that electrically contacts the layer 104. The contact resistance, denoted with $R_C$ may be proportional to the square root of the product of the sheet resistance, denoted with $R_S$, and the transition resistance, denoted with $\rho_C$, which can also be described by the following formula:

$$R_C = c \cdot \sqrt{R_S * \rho_C}$$

wherein c is a factor of proportionality. Therefore, a reduction of the sheet resistance $R_S$ of the layer 104 has a direct effect on the contact resistance $R_C$.

Figure 1B:
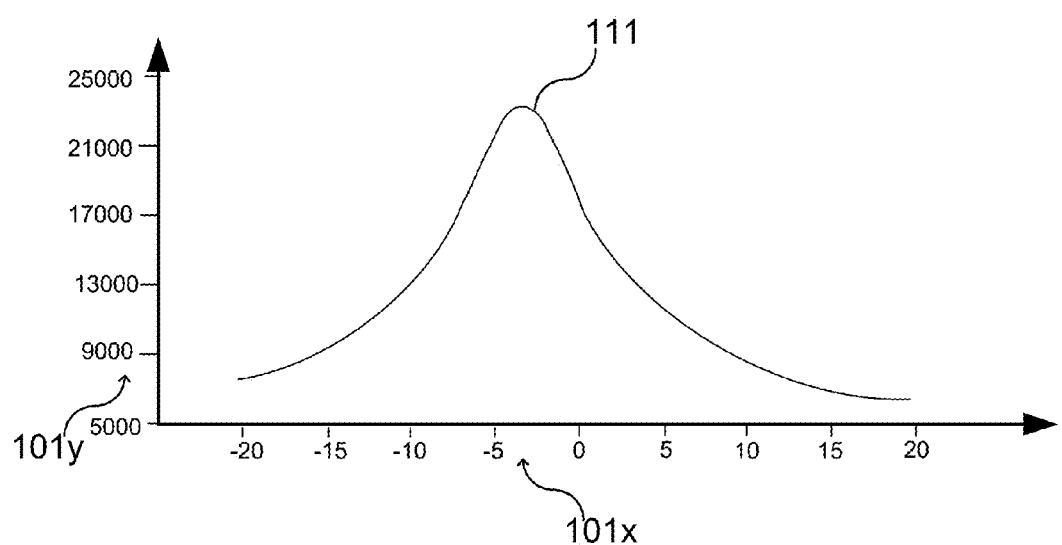
FIG. 1B shows a plot of the longitudinal resistance of a graphene layer on a silicon substrate as a function of substrate voltage.

FIG. 1B shows a plot 111 of the longitudinal resistance 101y (in other words the sheet resistance) of a graphene layer 104 on a silicon substrate 102 as a function of a voltage 101x applied to the substrate 102. The silicon substrate 102 may be covered with a (e.g. 300 nm thick) silicon oxide layer so that the graphene layer 104 is electrically isolated from the silicon substrate 102. As illustrated, the resistance of the graphene can be influenced, e.g. reduced, by applying an electrical field. However, in commonly used electronic devices, a voltage may be applied only through the entire back surface contact of the substrate, e.g. over the entire component (or in other words over the entire substrate). This may cause at least one of the following drawbacks: first, a voltage may need to be applied permanently on the component, which may lead to a high power loss, since the potential may be present over the whole chip area (in other words over the whole substrate area). This voltage may generally not match the voltages to be switched, so that a separate power supply may be necessary. Second, the graphene (or, in general, the layer including the two-dimensional material to be electrically contacted) may be influenced in every area over the whole substrate, including those areas, where it may be desired that the resistance of the graphene is not influenced. It may be for example desired to provide graphene with a preferably high resistance in a device region, e.g. for using the graphene as part of a sensor (or as a sensor structure), wherein the sensitivity of the sensor may be higher if the graphene has a higher resistance. The sensitivity of the sensor may be for example high, if the change of the resistance due to a change in the electrical field is high. In contrast, it may be for example also desired to provide graphene with a preferably low resistance in a contact region, e.g. for electrically contacting the graphene. A sensor based on graphene may be, for example, most sensitive if no electrical field or a predefined electrical field is provided that effects the resistance of the graphene layer, e.g. the sensor based on graphene may be most sensitive if no voltage is applied or if a small negative voltage (e.g. −5 V) is applied at the backside of the substrate on which the graphene is disposed. However, the optimum operating point for the sensor may be the point, where the change of the resistance is maximal.

In order to mitigate these effects, according to various embodiments, the structure of the chip may be adapted and/or fixed electrical charges (in other words localized electrical charges or a charge accumulation or a localized charge accumulation) may be provided in the vicinity of the contact areas of a two-dimensional material layer.

Figure 2A:
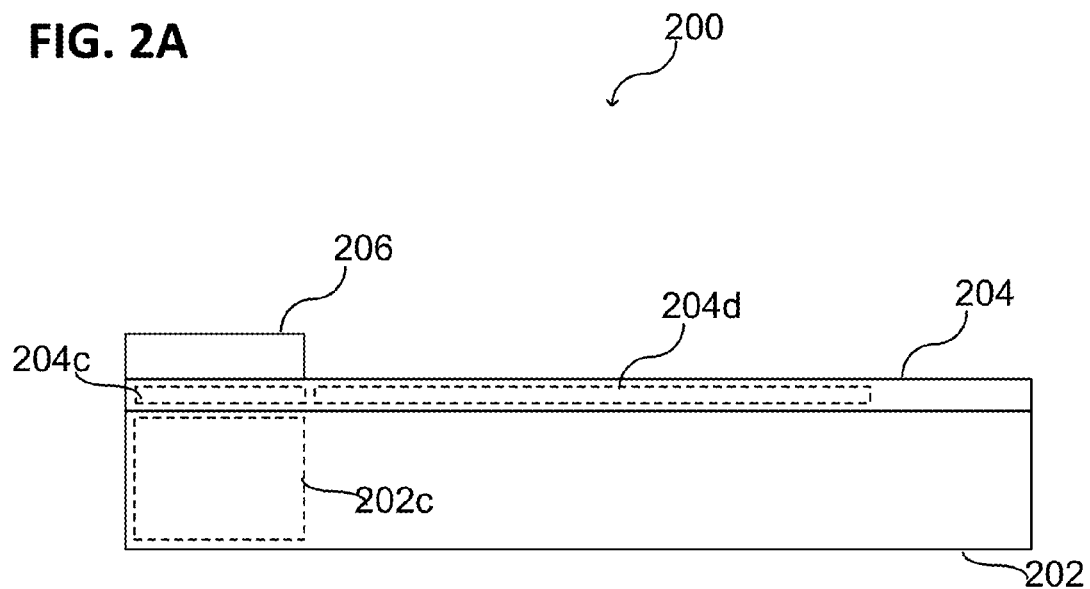
FIG. 2A shows an electronic device in a schematic cross sectional view, for illustrating aspects of various embodiments.

FIG. 2A illustrates an electronic device 200 in a schematic cross sectional view, for illustrating aspects of various embodiments. The electronic device 200 may include a layer 204 including or consisting of a two-dimensional material, also referred to as two-dimensional material layer 204. In various embodiments, a two-dimensional material may include or consist of graphene or a metal chalcogenide such as, for example, molybdenum disulphide, tungsten disulphide, or the like. In various embodiments, a two-dimensional material may include or consist of graphane, germanene, and the like.

The term "two-dimensional material" as used herein may, for example, be understood to include or refer to a material that crystallizes in a two-dimensional or planar structure, wherein a first geometric dimension (e.g. thickness) of the structure may be substantially smaller, e.g. at least two orders of magnitude smaller, e.g. at least three orders of magnitude smaller, e.g. at least four orders of magnitude smaller, or even smaller, than a second geometric dimension (e.g. length) and/or a third geometric dimension (e.g. width) of the structure. In one or more embodiments, the term "two-dimensional material" may be understood to include or refer to a material having the thinnest possible structure (one individual layer) derived from a material composed of several layers, e.g. a one carbon atom thick layer as for graphene, or a one $MoS_2$-unit thick layer as for $MoS_2$.

In accordance with one or more embodiments, a two-dimensional material layer 204 (e.g. a graphene layer 204) may have a thickness of less than or equal to about 200 nm, for example less than or equal to about 100 nm, for example less than or equal to about 80 nm, for example less than or equal to about 60 nm, for example less than or equal to about 40 nm, for example less than or equal to about 20 nm, for example in the range from about 0.5 nm to about 50 nm, for example about 0.34 nm (e.g. in case of a single monolayer of graphene).

In the case that the two-dimensional material layer 204 is a graphene layer, the graphene layer 204 may be formed, for example, with the use of one or more of the following processes in any of the electronic devices that will be described in more detail below:

aa) Exfoliation of graphene from graphite by sonication in solvents, e.g. organic solvents;

a) Chemical reduction of graphene oxide (e.g. exfoliated graphene oxide);

b) Chemical Vapor Deposition (CVD) of graphene;

c) Formation of graphene utilizing solid phase carbon sources;

d) Solid state epitaxial growth of graphene;

e) Process b), c), or d), as mentioned above, in combination with a transfer process onto the desired substrate (e.g. the carrier substrate, e.g. carrier membrane). Also direct growth may be possible on a dielectric substrate or on a dielectric layer by chemical vapor deposition through a catalytic metal film and subsequent removal of the metal film.

In the case that the two-dimensional material layer 204 is a graphene layer, the graphene layer 204 may include or consist of a plurality of crystallites or flakes that may, for example, have a size (e.g. diameter) of a few micrometers, e.g. about 1 µm. In various embodiments, the graphene layer 204 may be a continuous graphene layer that extends over the entire substrate. Each of the crystallites may include or consist of one or more platelets that may, for example, include or consist of a few layers of graphene, e.g. up to five layers, e.g. a monolayer, a bilayer, a trilayer, etc., of graphene, wherein a monolayer of graphene may have a two-dimensional structure with a thickness of about 0.34 nm. In one or more embodiments, the graphene layer may be a single monolayer of graphene.

Further, as illustrated in FIG. 2A, the electronic device 200 may include a dielectric structure 202, wherein the dielectric structure 202 may be disposed at a first side of the two-dimensional material layer 204. According to various embodiments, the dielectric structure 202 may be disposed below the two-dimensional material layer 204, as illustrated in FIG. 2A. In this case, the dielectric structure 202 may be or may include a dielectric substrate 202. Alternatively, the dielectric structure 202 may be disposed on any suitable carrier, e.g. on a semiconductor carrier. According to various embodiments, the dielectric structure 202 may be a surface layer of a semiconductor carrier. Alternatively, the dielectric structure 202 may be disposed over the two-dimensional material layer 204, as illustrated, for example, in FIGS. 3A and 3B. Furthermore, in various embodiments, the dielectric structure 202 may be made of dielectric material or may include dielectric material such as, for example, silicon oxide (e.g. $SiO_2$), silicon nitride (e.g. $Si_3N_4$), silicon carbide (SiC), aluminum oxide ($Al_2O_3$), hafnium oxide ($HfO_2$), or zirconium oxide ($ZrO_2$).

According to various embodiments, the dielectric structure 202 may include at least one contact region 202c. The at least one contact region 202c may define at least one contact area 204c of the two-dimensional material layer 204. Further, the least one contact region 202c may define a device area 204d of the two-dimensional material layer 204 adjacent to the at least one contact area 204c of the two-dimensional material layer 204. According to various embodiments, the at least one contact area 204c may be the region of the two-dimensional material layer 204 that is disposed over the at least one contact region 202c of the dielectric structure 202. The device area 204d of the two-dimensional material layer 204 may laterally surround the at least one contact area 204c of the two-dimensional material layer 204.

Further, as illustrated in FIG. 2A, the electronic device 200 may include at least one electrode 206 disposed at a second side of the two-dimensional material layer 204 opposite to the first side, wherein the at least one electrode 206 is in (e.g. direct) physical contact with the at least one contact area 204c of the two-dimensional material layer 204. According to various embodiments, the at least one electrode 206 may have substantially the same lateral extension as the at least one contact region 202c, wherein the contact area 204c of the two-dimensional material layer 204 may be the area that is arranged between the at least one electrode 206 and the at least one contact region 202c of the dielectric structure 202.

According to various embodiments, the at least one contact region 202c of the dielectric structure 202 may be different from the rest of the dielectric structure 202, or in other words, the dielectric structure 202 below the at least one contact area 204c (that means the at least one contact region 202c) may be different from the dielectric structure 202 below the device area 204d of the two-dimensional material layer 204. Illustratively, the dielectric structure 202 may be configured to adjust the contact resistance between the two-dimensional material layer 204 and the at least one electrode 206. The contact resistance shall be provided, for example, as low as possible. At the same time, the dielectric structure 202 may be configured to provide a device area 204d of the two-dimensional material layer 204 as desired, e.g. with predefined electrical properties differing from those provided in the at least one contact area 204c of the two-dimensional material layer 204. According to various embodiments, the electric characteristic of the two-dimensional material layer 204 shall be substantially influenced by the dielectric structure 202 only in the at least one contact area 204c. Alternatively, the electric characteristic in the at least one contact area 204c shall be provided to be different from the electric characteristic in the device area 204d of the two-dimensional material layer 204 by the dielectric structure 202.

The term "electric characteristic" used herein may be, for example, understood to include a physical property describing the electronic properties of the two-dimensional material, e.g. the electrical resistance (e.g. the sheet resistance), the electronic band structure (e.g. the band gap), the Fermi level, and the like.

According to various embodiments, the at least one contact region 202c of the dielectric structure 202 may be configured to adjust an electric characteristic of the two-dimensional material in the at least one contact area 204c of the layer 204 so that the electric characteristic of the two-dimensional material in the at least one contact area 204c of the layer 204 is different from the electric characteristic of the two-dimensional material in the device area 204d of the layer 204. Illustratively, the electric characteristic (e.g., a value or magnitude of the electric characteristic) of the two-dimensional material in the at least one contact area 204c of the layer 204 may be adjusted (or adapted or controlled) to provide a desired (e.g. a low) contact resistance.

According to various embodiments, the at least one contact region 202c of the dielectric structure 202 may be configured to adjust the work function of the material of the electrode 206 and/or of the two-dimensional material in the contact area 204c of the layer 204.

According to various embodiments, an electrical field may be provided that penetrates the layer 204 to adjust the electric characteristic of the two-dimensional material of the layer 204. The dielectric structure 202 may be configured to provide a predefined field strength distribution of the electrical field in the two-dimensional material layer 204.

According to various embodiments, the at least one contact region 202c of the dielectric structure 202 may be configured to generate an electrical field to adjust the electric characteristic of the two-dimensional material in the at least one contact area 204c of the layer 204. Therefore, the at least one contact region 202c of the dielectric structure 202 may include doped dielectric material, also referred to as fixed charges, localized charges or a charge accumulation, to provide the electrical field in the at least one contact area 204c of the layer 204 (or two provide the predefined field strength distribution of the electrical field in the two-dimensional material layer 204). Further, an electrically conductive portion that is electrically separated from the layer 204 (e.g. from the at least one contact area 204c and the device area 204d of the layer 204) may be provided in the dielectric structure 202 (e.g. in the contact region 202c of the dielectric structure 202) to provide the electrical field in the at least one contact area 204c of the layer 204 (or two provide the predefined field strength distribution of the electrical field in the two-dimensional material layer 204).

According to various embodiments, the dielectric structure 202 may be configured to provide a different electrical field (e.g. with a different field strength) in the contact area 204c of the layer 204 compared to the device area 204d of the layer 204.

Figure 2B:
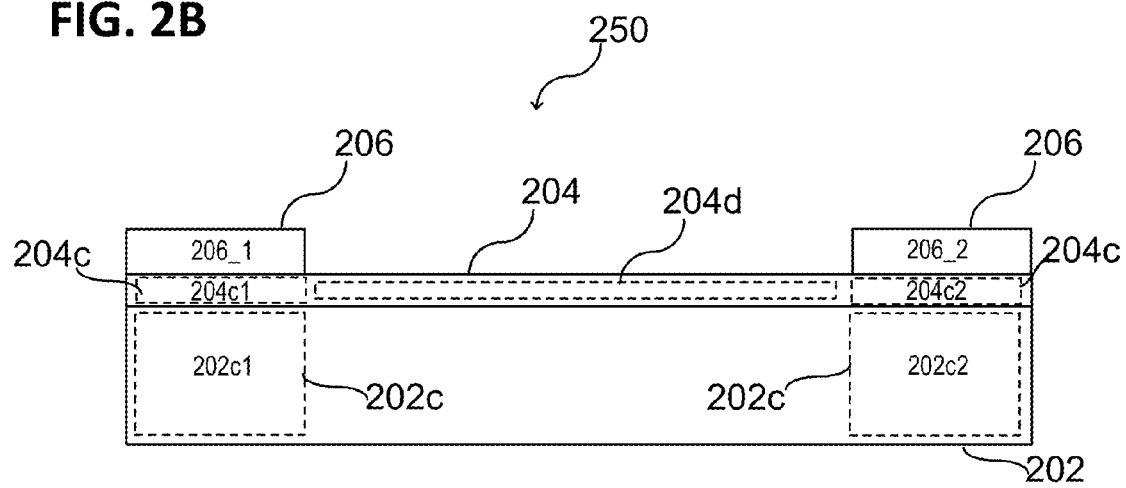
FIG. 2B shows an electronic device in a schematic cross sectional view, according to various embodiments.

FIG. 2B illustrates an electronic device 250 in a schematic cross sectional view, according to various embodiments, in analogy to the electronic device 200 illustrated in FIG. 2A. According to various embodiments, the at least one contact region 202c of the dielectric structure 202 may include two directly neighboring contact regions 202c that define two directly neighboring contact areas 204c of the two-dimensional material layer 204, wherein the device area 204d of the two-dimensional material layer 204 extends between the two directly neighboring contact areas 204c of the two-dimensional material layer 204. According to various embodiments, the device area 204d may be defined by the two directly neighboring contact areas 204c of the layer 204 that are electrically contacted by two directly neighboring electrodes 206. In other words, the device area 204d may be the part of the two-dimensional material layer 204 that is not covered with the electrodes 206 and that is not disposed over the contact regions 202c of the dielectric structure 202.

Figure 3A:
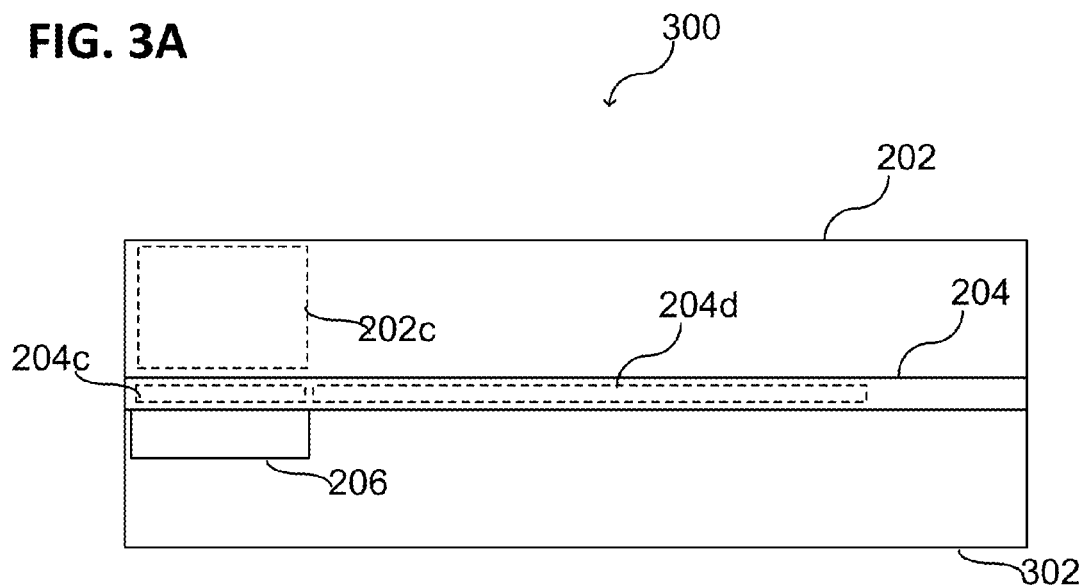
FIG. 3A shows an electronic device in a schematic cross sectional view, for illustrating aspects of various embodiments.
Figure 3B:
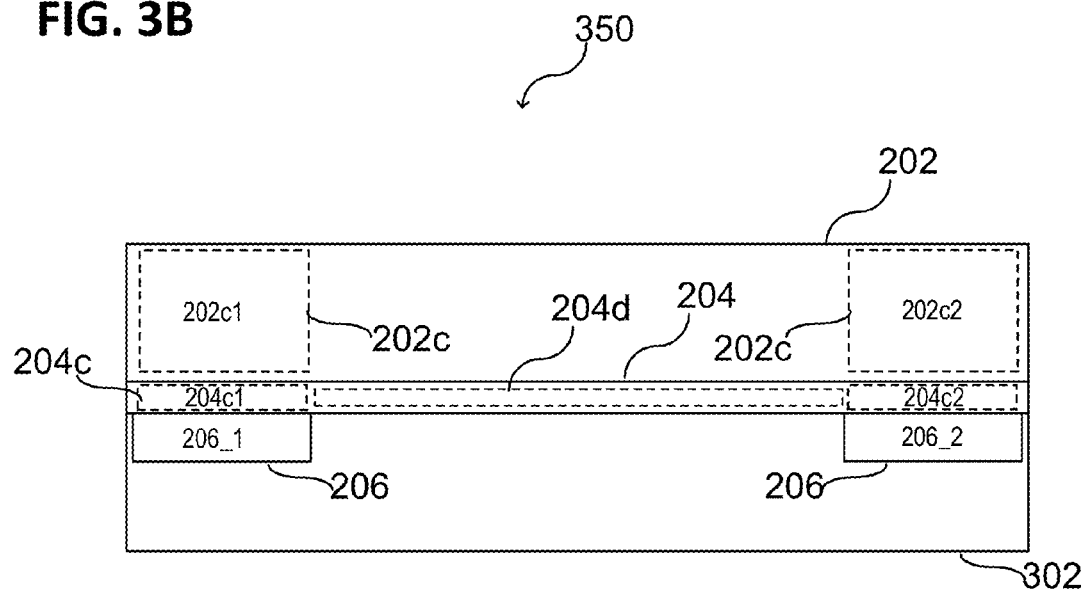
FIGS. 3B and 3C show respectively an electronic device in a schematic cross sectional view, according to various embodiments.

FIG. 3A illustrates an electronic device 300 in a schematic cross sectional view, for illustrating aspects of various embodiments, in analogy to the electronic device 200 illustrated in FIG. 2A, and FIG. 3B illustrates an electronic device 350 in a schematic cross sectional view, according to various embodiments, in analogy to the electronic device 250 illustrated in FIG. 2B. According to various embodiments, the at least one electrode 206, as illustrated in FIG. 3A, or the two directly neighboring electrodes 206, as illustrated in FIG. 3B, may be provided at least one of over and in a carrier 302, wherein the two-dimensional material layer 204 may be disposed over (e.g. directly on) the carrier 302 so that the one or more electrodes 206 may be in direct physical contact to the two-dimensional material layer 204. In this case, the dielectric structure 202 with the one or more contact regions may be disposed over (e.g. directly on) the two-dimensional material layer 204.

Figure 3C:
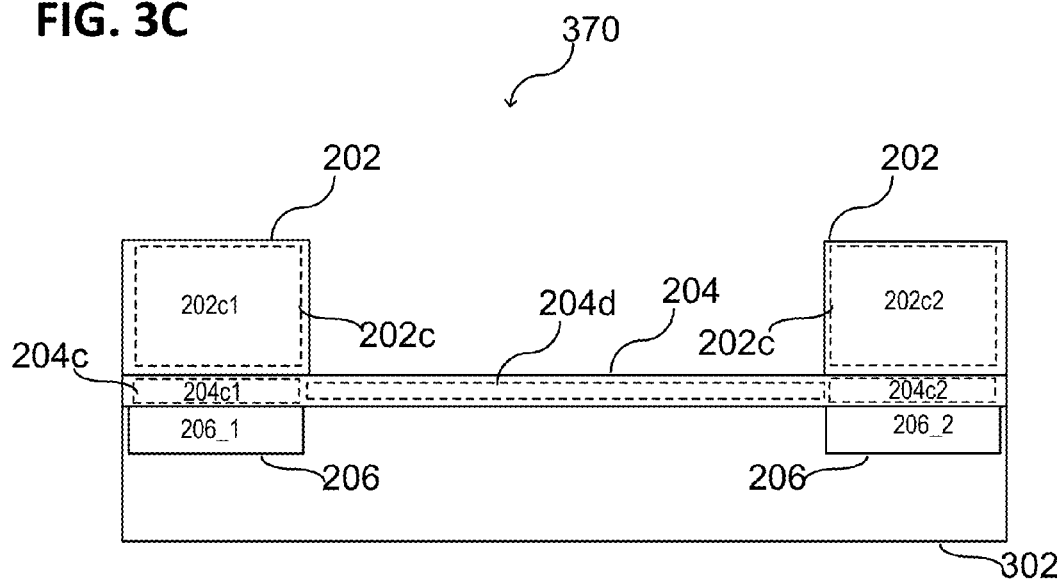

FIG. 3C illustrates an electronic device 370 in a schematic cross sectional view, according to various embodiments, in analogy to the electronic device 350 illustrated in FIG. 3B. According to various embodiments, a space between the two (e.g. directly neighboring) contact regions of the dielectric structure 202 may be free of any solid material. Illustratively, the device area 204d of the two-dimensional material layer 204 may be exposed. Therefore, according to various embodiments, the device area 204d of the two-dimensional material layer 204 may be used, for example, as a sensor.

According to various embodiments, the electronic device, as described herein, may be configured as any suitable electronic device, e.g. as a switch, a transistor, a sensor, a filter, a transmitter, a receiver, a transceiver, and the like. The two-dimensional material layer 204 may be a functional layer of the electronic device, e.g. including a two-dimensional material with a band gap.

According to various embodiments, the electronic device may be covered with an additional dielectric material or may include an additional dielectric material layer, e.g. the electronic device may be covered with a protection layer. According to various embodiments, the device area (e.g., 204d) of the two-dimensional material layer 204 of the electronic device may include or may be part of one or more passive and/or active elements such as, e.g., resistors, capacitors, transistors (e.g., bipolar transistors, field effect transistors, etc.), diodes, thyristors, or the like.

As illustrated in FIGS. 2B, 3B and 3C, according to various embodiments, an electronic device 250, 350, 370 may include: a layer 204 including a two-dimensional material (also referred to as two-dimensional material layer 204); a dielectric structure 202 at a first side of the layer 204, wherein the dielectric structure 202 includes a first contact region 202c1 and a second contact region 202c1 (or in other words at least two contact regions 202c), the first contact region 202c1 defining a first contact area 204c1 of the layer 204 and the second contact region 202c2 defining a second contact area 204c2 of the layer 204 (or in other words, the at least two contact regions 202c defining at least two contact areas 204c of the layer 204, respectively), and the first contact region 202c1 and the second contact region 202c2 further defining a device area 204d of the layer 204 between the first contact area 204c1 and the second contact area 204c2 of the layer 204; a first electrode 206_1 and a second electrode 206_2 (e.g. at least two electrodes 206 corresponding to the at least two contact areas 204c of the layer 204) disposed at a second side of the layer 204 opposite to the first side, wherein the first electrode 206_1 is in direct physical contact with the first contact area 204c1 of the layer 204 and wherein the second electrode 206_2 is in direct physical contact with the second contact area 204c2 of the layer 204, wherein the first contact region 202c1 and the second contact region 202c2 of the dielectric structure 202 are configured to adjust an electric characteristic of the two-dimensional material in the first contact area 204c1 and in the second contact area 204c2 of the layer, respectively, so that the electric characteristic of the two-dimensional material in the first contact area 204c1 and in the second contact area 204c2 of the layer 204 is different from the electric characteristic of the two-dimensional material in the device area 204d of the layer 204.

Figure 3D:
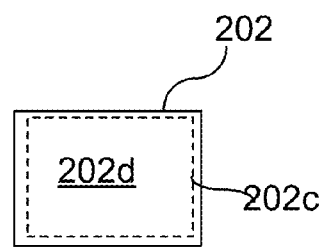
FIG. 3D shows a contact region of a dielectric structure in a schematic view, according to various embodiments.

FIG. 3D schematically illustrates a contact region 202c of the dielectric structure 202, according to various embodiments. The dielectric structure 202 may include or may consist of contact regions 202c, configured to influence the two-dimensional material layer 204 through an electrical field. Therefore, the respective contact region 202c may include p-type doped dielectric material 202d or n-type doped dielectric material 202d, also referred to as fixed charges 202d, localized charges 202d or a charge accumulation 202d. According to various embodiments, the doped dielectric material 202d defines the respective contact region 202c of the dielectric structure 202.

Figure 3E:
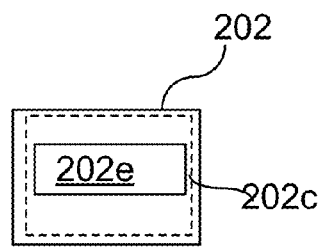
FIG. 3E shows a contact region of a dielectric structure in a schematic view, according to various embodiments.

FIG. 3E schematically illustrates a contact region 202c of the dielectric structure 202, according to various embodiments. The dielectric structure 202 may include or may consist of contact regions 202c, configured to influence the two-dimensional material layer 204 through an electrical field. Therefore, the respective contact region 202c may include at least one electrically conductive portion 202e. The at least one electrically conductive portion 202e may be, for example, buried in a dielectric layer so that the contact region 202c of the dielectric structure 202 is provided, as described herein. According to various embodiments, the at least one electrically conductive portion 202e defines the contact region 202c of the dielectric structure 202.

According to various embodiments, the electrically conductive portion 202e may be electrically separated from the two-dimensional material layer 204 (e.g. from the at least one contact area 204c and the device area 204d of the layer 204). Further, the electrically conductive portion 202e may include a metal, a doped (and therefore electrically conductive) semiconductor material, e.g. doped silicon, or any other electrically conductive material. The electrically conductive portion 202e may be electrically separated from the two-dimensional material layer 204 by a dielectric material portion.

Figure 4A:
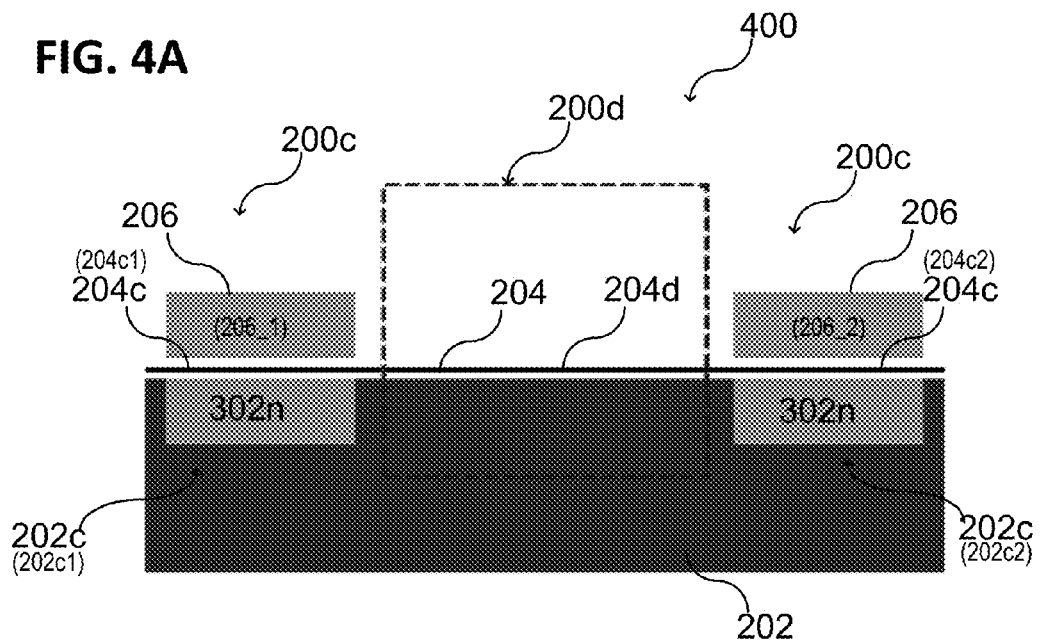
FIGS. 4A and 4B show respectively an electronic device in a schematic cross sectional view, according to various embodiments.
Figure 4B:
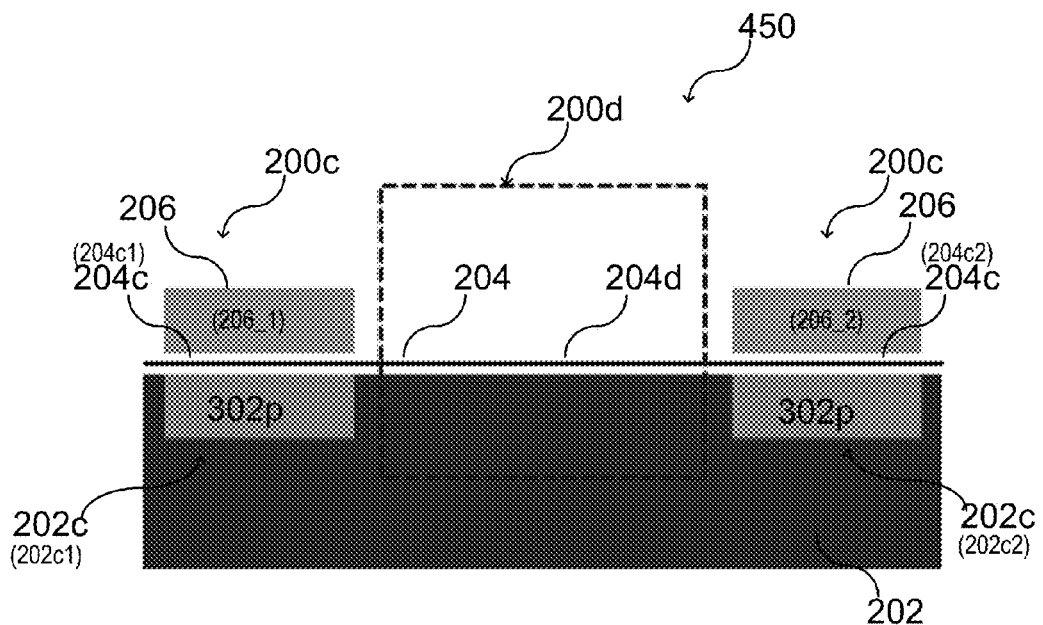

FIG. 4A and FIG. 4B illustrate an electronic device 400 and an electronic device 450, respectively, in a schematic view, according to various embodiments. Each of the electronic devices 400 and 450 includes a layer 204, wherein the layer 204 may include or may consist of a two-dimensional material (also referred to as two-dimensional material layer 204). Further, each of the electronic devices 400 and 450 includes a dielectric structure 202 disposed at a first side of the layer 204 (e.g. below the layer 204), wherein the dielectric structure 202 includes at least two contact regions 202c defining at least two contact areas 204c of the two-dimensional material layer 204, wherein the at least two contact regions 202c are spaced apart from each other (e.g. in the lateral direction) so that a device area 204d of the two-dimensional material layer 204 is provided between the at least two contact areas 204c of the two-dimensional material layer 204. According to various embodiments, the region of the dielectric structure 202 below the device area 204d of the two-dimensional material layer 204 may be free of the at least two contact regions 202c.

Further, each of the electronic devices 400 and 450 includes at least two electrodes 206 disposed at a second side of the two-dimensional material layer 204 opposite to the first side (e.g. over the layer 204, e.g. in direct physical contact with the two-dimensional material layer 204), the at least two electrodes 206 electrically contacting the at least two contact areas 204c of the two-dimensional material layer 204. According to various embodiments, each of the at least two contact regions 202c of the dielectric structure 202 includes or consists of a doped dielectric material 302n, 302p to adjust the electric characteristic of the two-dimensional material in the at least two contact areas 204c of the layer 204, wherein a space between the at least two contact regions 202c of the dielectric structure 202 is free of the doped dielectric material 302n, 302p. According to various embodiments, a region of the dielectric structure 202 below the device area 204d of the two-dimensional material layer 204 may be free of the doped dielectric material 302n, 302p.

Illustratively, each of the electronic devices 400 and 450 may include a device region 200d for providing any suitable electronic device based on the two-dimensional material layer 204, e.g. a sensor, a capacitor, a switch, a transistor, and the like, and each of the electronic devices 400 and 450 may include at least two contact regions 200c (e.g. including the at least two electrodes 206 and the doped dielectric material 302n, 302p for adjusting the contact resistance between the two-dimensional material layer 204 and the at least two electrodes 206).

According to various embodiments, the dielectric structure 202 may be partially doped, e.g. in the at least two contact regions 202c of the dielectric structure 202, with dopants of a conductivity type such as with dopants of a p conductivity type (which may also be referred to in the following as p-type dopants) or with dopants of an n conductivity type (which may also be referred to in the following as n-type dopants).

In the electronic device 400, as illustrated in FIG. 4A, the at least two contact regions 202c of the dielectric structure 202 may be doped with n-type dopants (the doped region is denoted by 302n) such as, for example, aluminum (Al). The dopants may be provided as fixed dielectric charge carriers within the dielectric material of the dielectric structure 202.

In the electronic device 450, as illustrated in FIG. 4B, the at least two contact regions 202c of the dielectric structure 202 may be doped with p-type dopants (the doped region is denoted by 302p) such as, for example, nitrogen (N) or cesium (Cs). The dopants may be provided as fixed dielectric charge carriers within the dielectric material of the dielectric structure 202.

The fixed dielectric charge carriers provided by the dopants (e.g. p-type or n-type dopants) may generate an electric field within the electronic device 400, 450, e.g. to influence the electric characteristic (e.g. the electric conductivity) of the contact areas 204c of the two-dimensional material layer 204. In various embodiments, the concentration or density of the dopants may be settable in a wide range. The dopants may be incorporated or implanted into the dielectric material (e.g. in-situ or after the deposition of the dielectric material) e.g. by means of a vapor deposition process such as e.g. a chemical vapor deposition process (CVD), e.g. an atomic layer deposition process (ALD), or a physical vapor deposition process (PVD), an ion implantation process. The atomic layer deposition process may provide a three-dimensionally smooth deposition (coating) together an extremely good dopant concentration control. The dopants (e.g. N or Cs) may be provided with a doping surface charge in the range from about of $10^{10}$ charge carriers per cm$^2$ to about $10^{14}$ charge carriers per cm$^2$.

According to various embodiments, as illustrated in FIGS. 4A and 4B, the at least two contact regions 202c of the dielectric structure 202 may include doped dielectric material of the same doping type. According to various embodiments, the dielectric structure 202 may be configured to provide substantially no electrical field in the one or more device areas 204d of the two-dimensional material layer 204. Alternatively, the dielectric structure 202 may be configured to provide a different electrical field in the one or more device areas 204d of the two-dimensional material layer 204 than in the one or more contact areas 204c of the two-dimensional material layer 204.

It has to be noted, that, only for better illustration, a gap is shown in FIGS. 4A and 4B between the electrodes 206 and the two-dimensional material layer 204 and between the two-dimensional material layer 204 and the dielectric structure 202; however, the electrodes 206 may be in physical contact with the two-dimensional material layer 204 and the two-dimensional material layer 204 may be in physical contact with the dielectric structure 202.

Figure 5A:
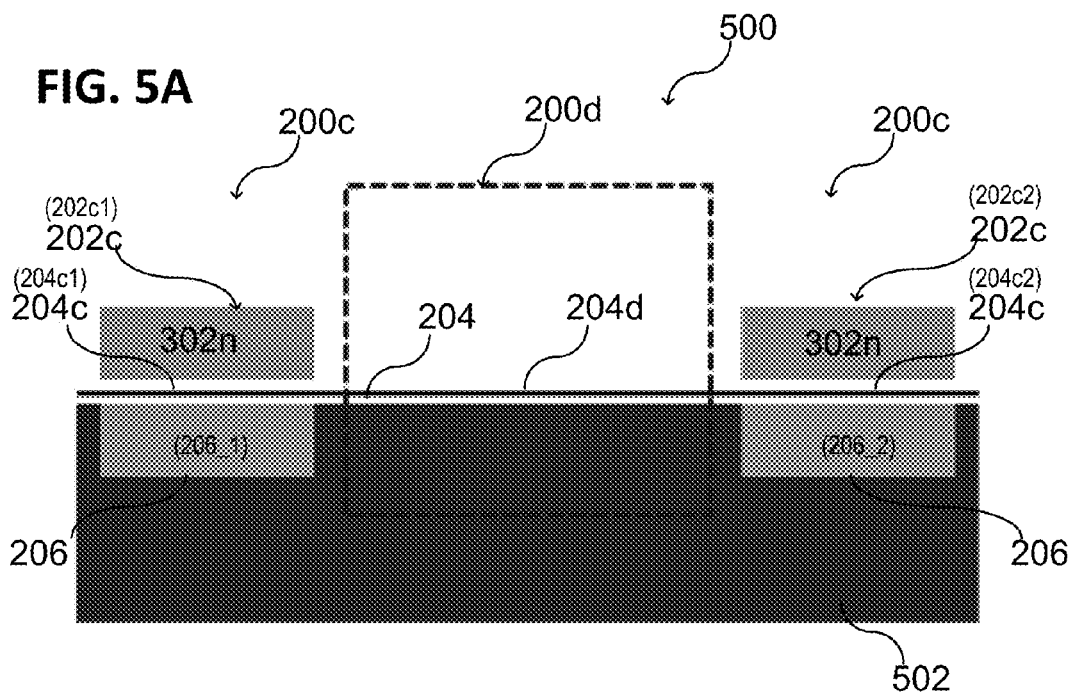
FIGS. 5A and 5B show respectively an electronic device in a schematic cross sectional view, according to various embodiments.
Figure 5B:
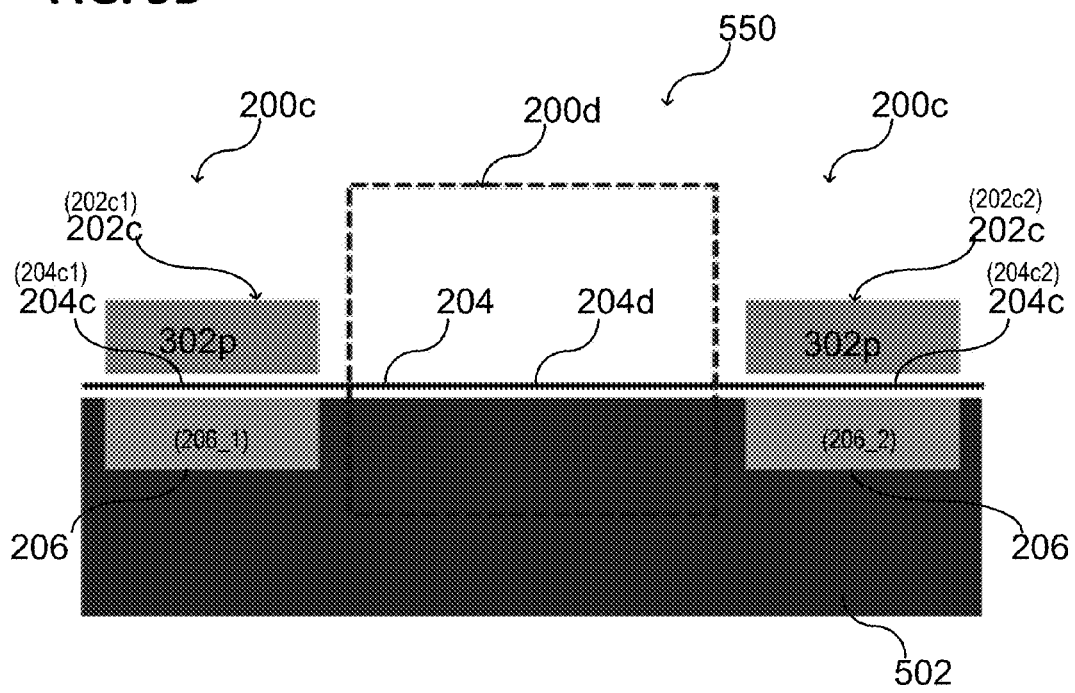

FIG. 5A and FIG. 5B illustrate an electronic device 500 and an electronic device 550, respectively, according to various embodiments, each of the electronic devices 500 and 550 including a layer 204; the layer 204 may include or may consist of a two-dimensional material (also referred to herein as two-dimensional material layer 204). Further, each of the electronic devices 500 and 550 includes a dielectric structure 202 disposed at a first side of the layer 204 (e.g. over the layer 204), wherein the dielectric structure 202 consists of at least two contact regions 202c defining at least two contact areas 204c of the layer 204, wherein the at least two contact regions 202c are spaced apart from each other (e.g. in the lateral direction) so that a device area 204d of the layer 204 is provided between the at least two contact areas 204c of the layer 204. According to various embodiments, the at least two contact regions 202c may consist of doped dielectric material 302n, 302p. According to various embodiments, a space between the at least two contact regions 202c may be free of doped dielectric material.

Further, each of the electronic devices 500 and 550 includes at least two electrodes 206 disposed at a second side of the layer 204 opposite to the first side (e.g. below the layer 204, e.g. buried in a dielectric carrier 502, wherein the at least two electrodes 206 may be in direct physical contact with the layer 204), the at least two electrodes 206 electrically contacting the at least two contact areas 204c of the layer 204. According to various embodiments, each of the at least two contact regions 202c include doped dielectric material 302n, 302p to adjust the electric characteristic of the two-dimensional material in the at least two contact areas 204c of the layer 204.

Illustratively, each of the electronic devices 500 and 550 may include a device region 200d for providing any suitable electronic device based on the two-dimensional material layer 204, e.g. a sensor, a capacitor, a switch, a transistor, and the like, and each of the electronic devices 500 and 550 may include at least two contact regions 200c (e.g. including the at least two electrodes 206 and the doped dielectric material 302n, 302p for adjusting the contact resistance of the at least two electrodes 206).

In the electronic device 500, as illustrated in FIG. 5A, the at least two contact regions 202c may be doped with n-type dopants such as, for example, aluminum (Al). The dopants may be provided as fixed dielectric charge carriers within the dielectric material of the dielectric structure 202.

In the electronic device 550, as illustrated in FIG. 5B, the at least two contact regions may be doped with p-type dopants such as, for example, nitrogen (N) or cesium (Cs). The dopants may be provided as fixed dielectric charge carriers within the dielectric material of the dielectric structure 202.

According to various embodiments, as illustrated in FIGS. 5A and 5B, the at least two contact regions 202c may include doped (e.g. permanently charged) dielectric material 302n, 302p of the same doping type respectively.

It has to be noted, that, only for better illustration, a gap is shown in FIGS. 5A and 5B between the electrodes 206 and the two-dimensional material layer 204 and between the two-dimensional material layer 204 and the at least two contact regions 202c of the dielectric structure 202; however, the electrodes 206 may be in physical contact with the two-dimensional material layer 204 and the two-dimensional material layer 204 may be in physical contact with the at least two contact regions 202c of the dielectric structure 202.

As illustrated in FIGS. 4A and 4B and FIGS. 5A and 5B, according to various embodiments, an electronic device 400, 450, 500, 550 may include: a layer 204 including a two-dimensional material (also referred to as two-dimensional material layer 204), a dielectric structure 202 disposed at a first side of the layer 204, wherein the dielectric structure 202 includes a first contact region 202c1 and a second contact region 202c2 (e.g. at least two contact regions 202c) defining a first contact area 204c1 and a second contact area 204c2 (e.g. at least two contact areas 204c) of the layer 204, respectively, wherein the first contact region 202c1 and the second contact region 202c2 are spaced apart from each other so that a device area 204d of the layer 204 is provided between the first contact area 204c1 and the second contact area 204c2 of the layer 204; a first electrode 206_1 and a second electrode disposed 206_2 (e.g. at least two electrodes 206 corresponding to the at least two contact areas 204c) at a second side of the layer 204 opposite to the first side, the first electrode 206_1 and the second electrode 206_2 electrically contacting the first contact area 204c1 and the second contact area 204c2 of the layer 204, respectively; wherein the first contact region 202c1 and second contact region 202c2 of the dielectric structure 202 include a doped dielectric material 302n, 302p to adjust an electric characteristic of the two-dimensional material in the first contact area 204c1 and in the second contact area 204c2 of the layer 204, respectively, wherein a space between the first contact region 202c1 and the second contact region 202c2 of the dielectric structure 202 corresponding to the device area 204d of the layer 204 is free of the doped dielectric material.

Figure 6A:
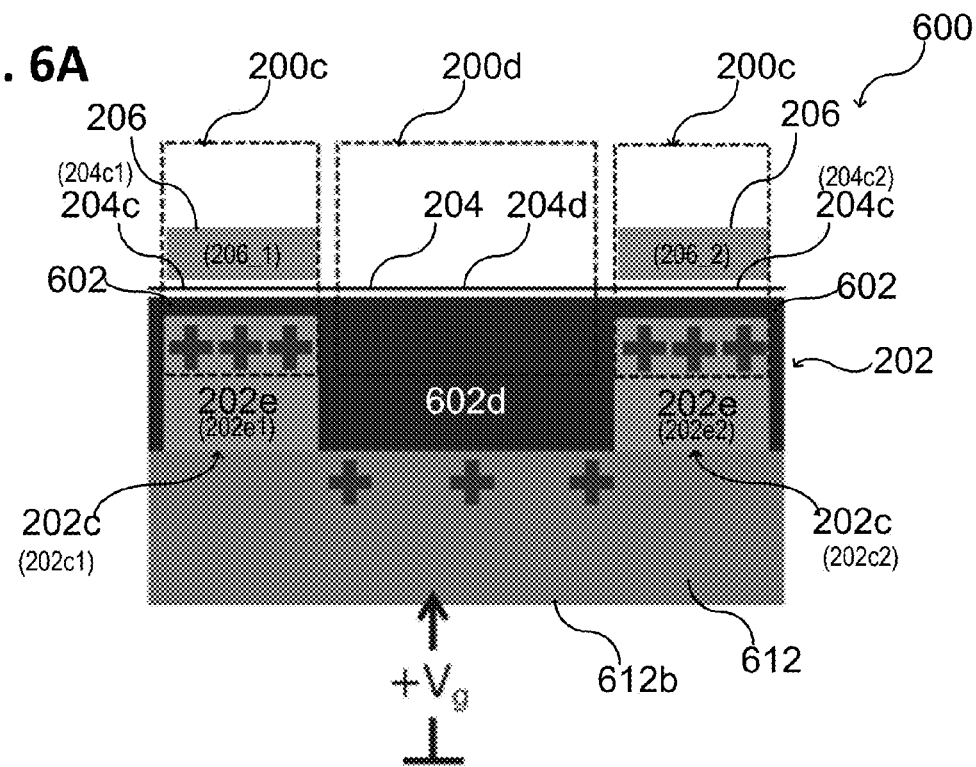
FIGS. 6A and 6B show respectively an electronic device in a schematic cross sectional view, according to various embodiments.
Figure 6B:
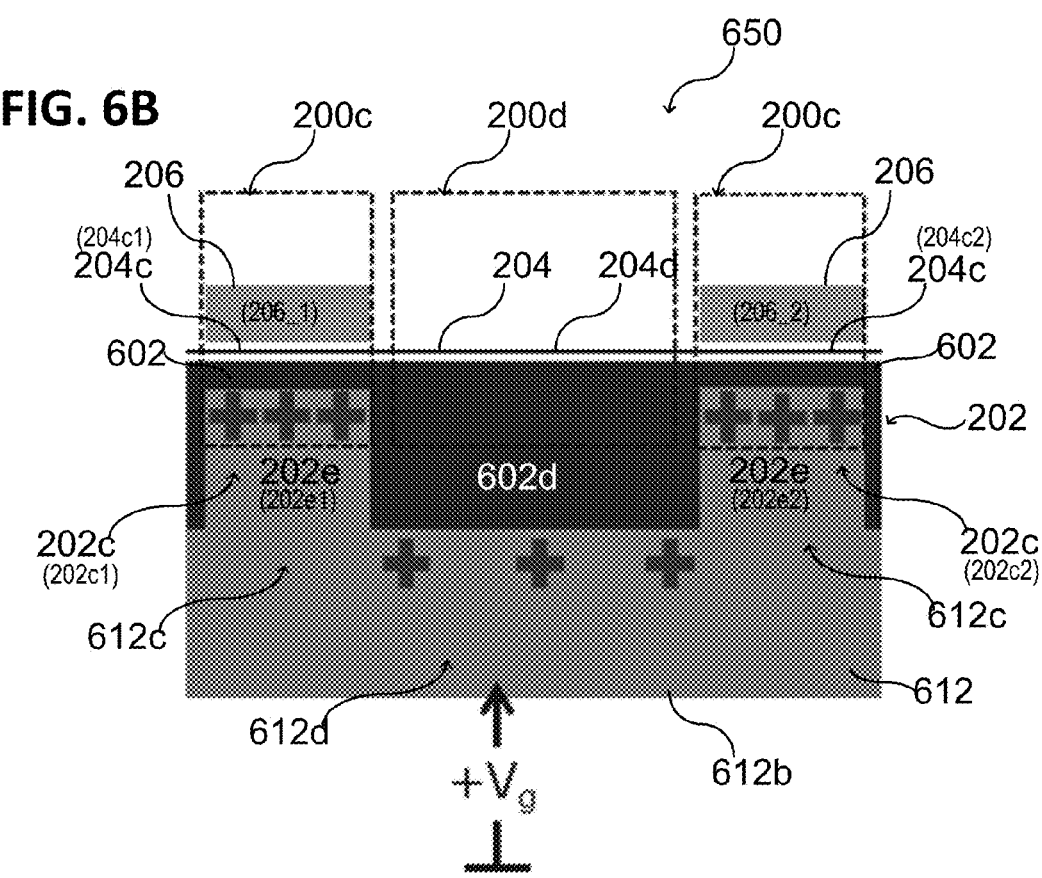

FIG. 6A and FIG. 6B illustrate an electronic device 600 and an electronic device 650, respectively, according to various embodiments. Each of the electronic devices 600 and 650 includes a layer 204, the layer 204 including or consisting of a two-dimensional material, also referred to as two-dimensional material layer 204. Further, each of the electronic devices 600 and 650 includes a dielectric structure disposed 202 at a first side of the two-dimensional material layer 204, wherein the dielectric structure 202 includes at least two contact regions 202c defining at least two contact areas 204c of the two-dimensional material layer 204, wherein the at least two contact regions 202c are spaced apart from each other so that a device area 204d of the two-dimensional material layer 204 is provided between the at least two contact areas 204c of the two-dimensional material layer 204. Each of the electronic devices 600 and 650 further includes at least two electrodes 206 disposed at a second side of the two-dimensional material layer 204 opposite to the first side, the at least two electrodes 206 electrically contacting the at least two contact areas 204c of the two-dimensional material layer 204. According to various embodiments, each of the at least two contact regions 202c of the dielectric structure 202 includes an electrically conductive portion 202e that is electrically separated from the contact area 204c of the two-dimensional material layer 204 to adjust the electric characteristic of the two-dimensional material in the at least two contact areas 204c of the two-dimensional material layer 204 by applying a voltage (denoted with $+V_g$) at the electrically conductive portion 202e.

Illustratively, each of the electronic devices 600 and 650 may include at least two contact regions 200c, wherein the electrodes 206 and the electrically conductive portions 202e may be disposed in the contact regions 200c of the electronic device 600, 650 or wherein the electrodes 206 and the electrically conductive portions 202e define the respective contact regions 200c of the electronic device 600, 650, and wherein the electronic device 600, 650 may include a device region 200d between the at least two contact regions 200c.

According to various embodiments, each of the electrically conductive portions 202e may include or may consist of a metal and/or a doped (e.g. electrically conductive) semiconductor material. As illustrated in FIG. 6A, in the electronic device 600 the dielectric structure 202 including the electrically conductive portions 202e in the at least two contact regions 202c may be disposed over a carrier 612. The carrier 612 may include electrically conductive material, e.g. doped silicon. Therefore, a voltage $+V_g$ that is applied at the backside 612b of the carrier 612 (or in general a voltage that is provided to the carrier 612) may induce charges into the electrically conductive portions 202e, wherein the charges (denoted with + for a positive voltage that is applied to the carrier 612) may generate the electrical field in the contact areas 204c of the two-dimensional material layer 204 to adjust the contact resistance between the contact areas 204c of the two-dimensional material layer 204 and the respective electrodes 206. According to various embodiments, also a negative voltage (denoted with $-V_g$) may be applied to the carrier 612 and therefore to the electrically conductive portions 202e.

According to various embodiments, the electrically conductive portions 202e (that are for example embedded in the dielectric material 602 of the dielectric structure 202) may be electrically separated (in other words isolated) from the contact areas 204c of the two-dimensional material layer 204.

According to various embodiments, an electronic circuit may be electrically coupled to each of the electrically conductive portions 202e, e.g. through the electrically conductive carrier 612, wherein the electronic circuit may be configured to apply a voltage $+V_g$ to each of the electrically conductive portions 202e.

According to various embodiments, a metallization structure may be used to electrically contact each of the electrically conductive portions 202e. In this case, the carrier 612 can also be made of electrically insulating material.

According to various embodiments, the region between the at least two contact regions 202c of the dielectric structure 202 may be filled with (undoped) dielectric material. In other words, the device area 204d of the two-dimensional material layer 204 may not be substantially influenced by the voltage $+V_g$ (or $-V_g$) provided to the electrically conductive portions 202e. In other words, the space between the at least two contact regions 202e of the dielectric structure 202 may be free of electrically conductive material coupled to a power source.

The electronic device 650 illustrated in FIG. 6B has a similar dielectric structure 202 as shown in FIG. 6A, according to various embodiments. Here, an electrically conductive carrier 612 or an electrically conductive layer 612 may be patterned so that the electrically conductive portions 202e may be provided. The electrically conductive carrier 612 or the electrically conductive layer 612 may be separated from the two-dimensional material layer 204 by dielectric material 602.

The electronic device 650 of FIG. 6B includes a patterned electrically conductive layer structure 612; and the patterned electrically conductive layer structure 612 includes or consists of a first region 612c (e.g. arranged below contact regions 202c of the dielectric structure 202) and a second region 612d (e.g. arranged below the device region 202d of the dielectric structure 202) adjacent to each other. Illustratively, the electronic device 650 includes a contact region 200c and a device region 200d, wherein the patterned electrically conductive layer structure 612 defines the contact area 204c of the two-dimensional material layer 204 in the contact region 200c of the electronic device 200 and the device area 204d of the two-dimensional material layer 204 in the device region 200d of the electronic device 650. Further, a dielectric layer 602 is disposed between the patterned electrically conductive layer structure 612 and the two-dimensional material layer 204. According to various embodiments, the dielectric layer 602 has a first thickness between the first region 612c of the patterned electrically conductive layer structure 612 and the first area 204c of the two-dimensional material layer 204 and a second thickness between the second region 612d of the patterned electrically conductive layer structure 612 and the second region 204d of the two-dimensional material layer 204, wherein the first thickness is different from the second thickness (e.g. the first thickness may be greater or smaller than the second thickness). In other words, since the electrically conductive portions 202e may be part of the patterned electrically conductive layer structure 612, the dielectric layer 602 has a first thickness between the first region 202e of the patterned electrically conductive layer structure 612 and the first area 204c of the two-dimensional material layer 204 and a second thickness between the second region 612d of the patterned electrically conductive layer structure 612 and the second region 204d of the two-dimensional material layer 204, wherein the first thickness is different from the second thickness (e.g. the first thickness may be greater or smaller than the second thickness). According to various embodiments, both regions 612c, 612d of the electrically conductive layer structure 612 may be electrically conductive or in other words may include or may consist of electrically conductive material.

According to various embodiments, the thickness of the dielectric layer 602 between the first region 612c (or 202e) of the patterned electrically conductive layer structure 612 and the first area 204c of the two-dimensional material layer 204 may be in the range from about 3 nm to about 3000 nm, e.g. in the range from about 3 nm to about 2000 nm, e.g. in the range from about 3 nm to about 1000 nm. According to various embodiments, the thickness of the dielectric layer 602 between the second region 612d of the patterned electrically conductive layer structure 612 and the second area 204d of the two-dimensional material layer 204 may be in the range from about 300 nm to about 5 µm.

Further, the patterned electrically conductive layer structure 612 may be electrically coupled to a contact (e.g. a backside contact) for applying an electrical voltage +$V_g$ to the patterned electrically conductive layer structure 612. The patterned electrically conductive layer structure 612 may provide the electrically conductive portions 202e so that together with the dielectric layer 602 the dielectric structure 202 is provided, as described before.

According to various embodiments, the first region 612c of the patterned electrically conductive layer structure 612 (e.g. provided in the contact region 200c of the electronic device 650) may be electrically isolated (in other words separated) from the second region 612d of the patterned electrically conductive layer structure 612 (e.g. provided in the device region 200d of the electronic device 650), e.g. via a trench filled with electrically insulating material or via a portion of an electrically insulating material (not illustrated).

As illustrated in FIGS. 6A and 6B, the effect of charge transfer in the device area 204d of the two-dimensional material layer 204 may be reduced by using different thicknesses for the dielectric material 602 disposed between the electrically conductive material 202e, 612 and the two-dimensional material layer 204. Illustratively, the electrical potential in the device area 204d of the two-dimensional material layer 204 may be controlled by the thickness of the dielectric material 602 on which the two-dimensional material layer 204 is disposed. The thinner the dielectric material 602 the higher the electrical field that can be induced into the two-dimensional material layer 204.

It has to be noted, that, only for better illustration, a gap is shown in FIGS. 6A and 6B between the electrodes 206 and the two-dimensional material layer 204 and between the two-dimensional material layer 204 and the dielectric material 602 of the dielectric structure 202; however, the electrodes 206 may be in physical contact with the two-dimensional material layer 204 and the two-dimensional material layer 204 may be in physical contact with the dielectric material 602 of the dielectric structure 202.

As illustrated in FIGS. 6A and 6B, according to various embodiments, an electronic device 600, 650 may include: a layer 204 including a two-dimensional material (also referred to as two-dimensional material layer 204), a dielectric structure 202 disposed at a first side of the layer 204, wherein the dielectric structure includes a first contact region 202c1 and a second contact region 202c2 (e.g. at least two contact regions 202c) defining a first contact area 204c1 and a second contact area 204c2 (e.g. at least two contact areas 204c) of the layer 204, respectively, wherein the first contact region 202c1 and the second contact region 202c2 are spaced apart from each other so that a device area 204d of the layer 204 is provided between the first contact area 204c1 and the second contact area 204c2 of the layer 204; a first electrode 206_1 and a second electrode 206_2 (e.g. at least two electrodes 206 corresponding to the at least two contact areas 204c) disposed at a second side of the layer 204 opposite to the first side, the first electrode 206_1 and the second electrode 206_2 electrically contacting the first contact area 204c1 and the second contact area 204c2 of the layer 204, respectively; wherein the first contact region 202c1 and the second contact region 202c2 of the dielectric structure 202 include a first electrically conductive portion 202e1 and a second electrically conductive portion 202e2 (e.g. at least two electrically conductive portions 202e corresponding to the at least two contact areas 204c of the layer 204), respectively, wherein the first electrically conductive portion 202e1 and the second electrically conductive portion 202e2 are electrically separated from the layer 204 to adjust an electric characteristic of the two-dimensional material in the first contact area 204c1 and in the second contact area 204c2 of the layer 204 by applying a voltage +$V_g$ at the first electrically conductive portion 202e1 and at the second electrically conductive portion 202e2, and wherein a device region 602d is disposed between the first contact region 202c1 and the second contact region 202c2 of the dielectric structure 202 corresponding to the device area 204d of the layer 204, the device region 602d including dielectric material.

Figure 7A:
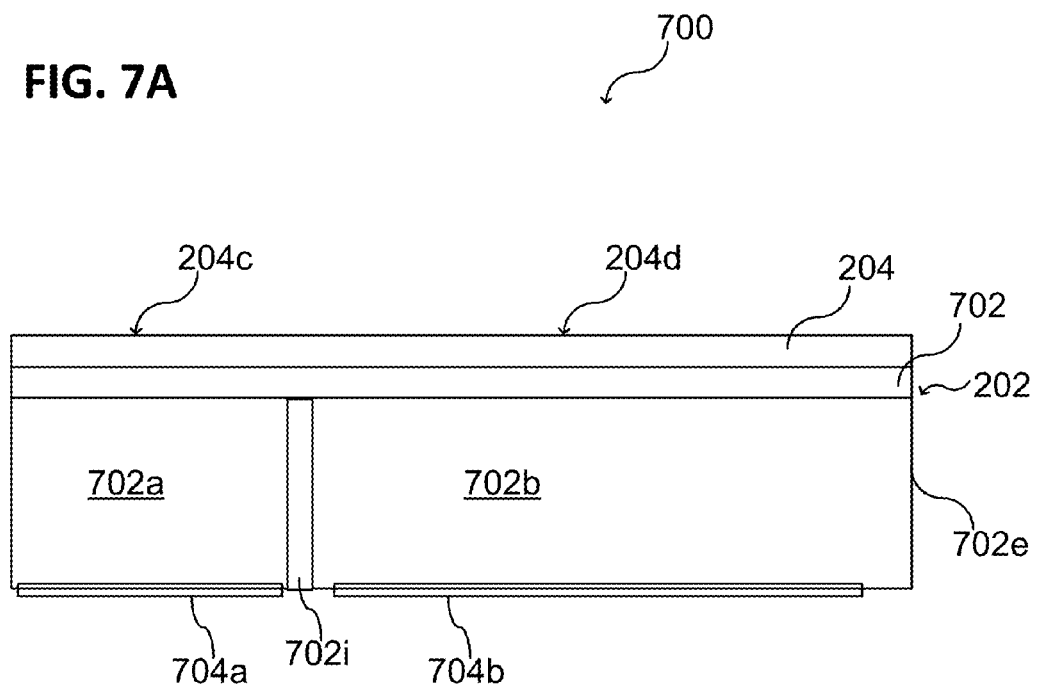
FIGS. 7A and 7B show respectively an electronic device in a schematic cross sectional view, according to various embodiments.

FIG. 7A illustrates an electronic device 700, according to various embodiments. The electronic device 700 includes an electrically conductive layer 702e; the electrically conductive layer 702e includes at least a first region 702a and a second region 702b, wherein the first region 702a and the second region 702b are electrically isolated from each other. According to various embodiments, an electrical isolation structure 702i may be provided between the first region 702a and the second region 702b of the electrically conductive layer 702e. The electrical isolation structure 702i may include or may be a trench filled with electrically insulating material. According to various embodiments, the electrical isolation structure 702i may include or may be a portion of an electrically insulating material. The electrical isolation structure 702i may extend completely though the electrically conductive layer 702e.

Further, according to various embodiments, the electronic device 700 includes a dielectric layer 702 disposed over the electrically conductive layer 702e. Illustratively, the dielectric layer 702, the electrically conductive layer 702e, and the electrical isolation structure 702i provide the dielectric structure 202, as described before. Further, according to various embodiments, the electronic device 700 includes a two-dimensional material layer 204 disposed over the dielectric layer 702, the two-dimensional material layer 204 includes a first area 204c disposed over the first region 702a of the electrically conductive layer 702e and a second area 204d disposed over the second region 702b of the electrically conductive layer 702e. According to various embodiments, the first area 204c of the two-dimensional material layer 204 may be a contact area and the second area 204d may be a device area, as described before. Illustratively, the first area 204c of the two-dimensional material layer 204 may be influenced by the first region 702a of the electrically conductive layer 702e and the second area 204d of the two-dimensional material layer 204 may be influenced by the second region 702b of the electrically conductive layer 702e. Since the first region 702a and the second region 702b are electrically separated from each other, the first area 204c and the second area 204d of the two-dimensional material layer 204 may be controlled (or adjusted) independently from each other by applying a predefined voltage to the respective region 702a, 702b of the electrically conductive layer 702e.

Therefore, the first region 702a of the electrically conductive layer 702e may be electrically coupled to a first contact 704a for applying a first electrical voltage to the first region 702a, e.g. to provide a first electrical field in the first area 204c of the two-dimensional material layer 204. Further, the second region 702b of the electrically conductive layer 702e may be electrically coupled to a second contact 704b for applying a second electrical voltage to the second region 702b, e.g. to provide a second electrical field in the second area 204d of the two-dimensional material layer 204. According to various embodiments, the first voltage may be different from the second voltage.

As illustrated in FIG. 7A, at least two support electrodes 702a, 702b may be provided below the two-dimensional material layer 204, the at least two support electrodes 702a, 702b may be electrically separated from each other and from the two-dimensional material layer 204. Therefore, different areas of the two-dimensional material layer 204 may be influenced by applying a voltage to the respective support electrode 702a, 702b.

The first contact 704a and the second contact 704b may be disposed at the backside of the electronic device 700, e.g. as backside contacts or backside contact pads. Alternatively, the first contact 704a and the second contact 704b may be disposed at the front side of the electronic device 700, e.g. as front side contacts or front side contact pads. According to various embodiments, the at least two support electrodes 702a, 702b (in other words the first region 702a and the second region 702b of the electrically conductive layer 702e) may be part of a metallization structure.

According to various embodiments, a driver circuit may be coupled to the first contact 704a and the second contact 704b for applying the predefined voltage for each of the regions 702a, 702b respectively.

Figure 7B:
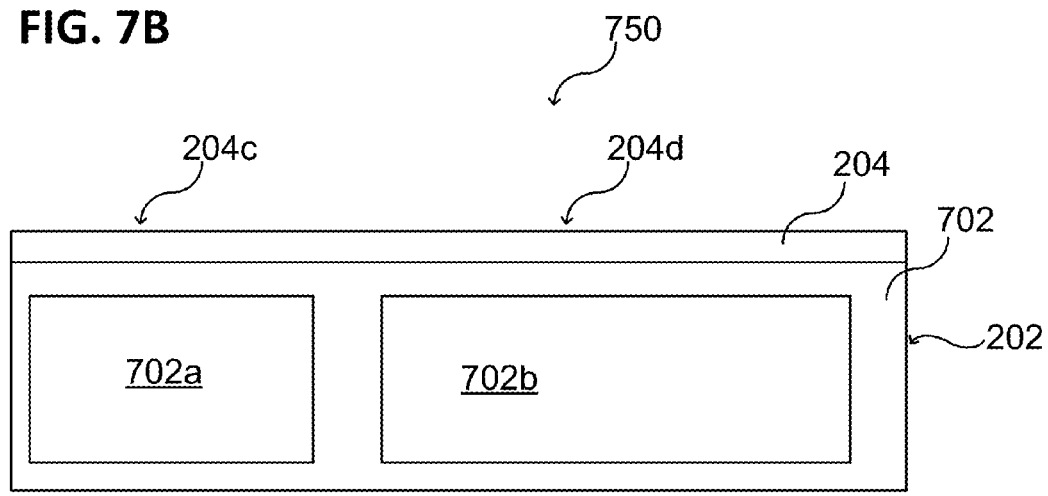

According to various embodiments, FIG. 7B illustrates a similar electronic device 750 as shown in FIG. 7A, according to various embodiments. As illustrated in FIG. 7B, at least two support electrodes 702a, 702b may be provided at a first side of a two-dimensional material layer 204 (e.g. over the two-dimensional material layer 204 or below the two-dimensional material layer 204), the at least two support electrodes 702a, 702b may be electrically separated from each other and from the two-dimensional material layer 204. In other words, the at least two support electrodes 702a, 702b may be buried in a dielectric layer 702. Therefore, different areas 204a, 204d of the two-dimensional material layer 204 may be influenced by applying a voltage to the respective support electrode 702a, 702b. According to various embodiments, a driver circuit may be coupled (e.g. via a metallization structure) to the respective support electrode 702a, 702b for applying a predefined voltage for each of the support electrodes 702a, 702b respectively.

According to various embodiments, an electronic device may include: a layer including a two-dimensional material; a dielectric structure at a first side of the layer, wherein the dielectric structure includes a first contact region and a second contact region, the first contact region defining a first contact area of the layer and the second contact region defining a second contact area of the layer, and the first contact region and the second contact region further defining a device area of the layer between the first contact area and the second contact area of the layer; a first electrode and a second electrode disposed at a second side of the layer opposite to the first side, wherein the first electrode is in direct physical contact with the first contact area of the layer and wherein the second electrode is in direct physical contact with the second contact area of the layer, wherein the first contact region and the second contact region of the dielectric structure are configured to adjust an electric characteristic of the two-dimensional material in the first contact area and in the second contact area of the layer, respectively, so that the electric characteristic of the two-dimensional material in the first contact area and in the second contact area of the layer is different from the electric characteristic of the two-dimensional material in the device area of the layer.

According to various embodiments, the electronic device 200 may include one or more additional contacts or additional electrodes. In other words, the electronic device 200 may include the first electrode, the second electrode, and at least one additional electrode. The at least one additional electrode may or may not be in direct contact with the layer including the two-dimensional material.

According to various embodiments, the first contact region and the second contact region of the dielectric structure may be configured to adjust the electrical resistance (or in other word the value of the electrical resistance) of the two-dimensional material in the first contact area and in the second contact area of the layer, respectively, so that the electrical resistance of the two-dimensional material in the first contact area and in the second contact area of the layer is different from the electrical resistance of the two-dimensional material in the device area of the layer.

According to various embodiments, the device area of the layer is free of further electrodes that are in direct physical contact with the layer.

According to various embodiments, the first contact region and the second contact region of the dielectric structure are configured to generate an electrical field to adjust the electric characteristic of the two-dimensional material in the first contact area and in the second contact area of the layer, respectively. Illustratively, the generated electrical field may adjust the electrical resistance (or in other word the value of the electrical resistance) of the two-dimensional material in the first contact area and in the second contact area of the layer, respectively.

According to various embodiments, the first contact region and the second contact region of the dielectric structure each include doped dielectric material. The doped dielectric material may generate the electrical field to adjust the electric characteristic of the two-dimensional material in the first contact area and in the second contact area of the layer, respectively. According to various embodiments, the first contact region and the second contact region of the dielectric structure may include the same doped dielectric material or may include different doped dielectric material.

According to various embodiments, the first contact region includes a first electrically conductive portion and the second contact region of the dielectric structure includes a second electrically conductive portion, wherein the first electrically conductive portion and the second electrically conductive portion are electrically separated from the layer.

According to various embodiments, the first contact region and the second contact region of the dielectric structure are configured to provide the same electric characteristic (e.g. the same value of the electrical resistance) of the two-dimensional material in the first contact area and in the second contact area of the layer.

According to various embodiments, the first contact region and the second contact region of the dielectric structure are configured to provide different electric characteristics (e.g. different values of the electrical resistance) of the two-dimensional material in the first contact area and in the second contact area of the layer.

According to various embodiments, the two-dimensional material includes graphene.

According to various embodiments, the layer includes a monolayer of the two-dimensional material.

According to various embodiments, an electronic device may include: a layer including a two-dimensional material, a dielectric structure disposed at a first side of the layer, wherein the dielectric structure includes a first contact region and a second contact region defining a first contact area and a second contact area of the layer, respectively, wherein the first contact region and the second contact region are spaced apart from each other so that a device area of the layer is provided between the first contact area and the second contact area of the layer; a first electrode and a second electrode disposed at a second side of the layer opposite to the first side, the first electrode and the second electrode electrically contacting the first contact area and the second contact area of the layer, respectively; wherein the first contact region and second contact region of the dielectric structure include a doped dielectric material to adjust an electric characteristic of the two-dimensional material in the first contact area and in the second contact area of the layer, respectively, wherein a space between the first contact region and the second contact region of the dielectric structure corresponding to the device area of the layer is free of the doped dielectric material.

According to various embodiments, the first electrode and the second electrode are at least partially embedded in a dielectric layer, wherein the layer is disposed on the dielectric layer, and wherein the dielectric structure is disposed over the layer.

According to various embodiments, the dielectric layer is disposed on a semiconductor carrier.

According to various embodiments, the dielectric structure is disposed on a semiconductor carrier; wherein the space between the first contact region and the second contact region of the dielectric structure is filled with dielectric material, wherein the layer is disposed over the dielectric structure, and wherein the first electrode and the second electrode are disposed over the layer.

According to various embodiments, the dielectric material disposed in the space between the first contact region and the second contact region of the dielectric structure includes undoped dielectric material.

According to various embodiments, the two-dimensional material includes graphene.

According to various embodiments, an electronic device may include: a layer including a two-dimensional material, a dielectric structure disposed at a first side of the layer, wherein the dielectric structure includes a first contact region and a second contact region defining a first contact area and a second contact area of the layer, respectively, wherein the first contact region and the second contact region are spaced apart from each other so that a device area of the layer is provided between the first contact area and the second contact area of the layer; a first electrode and a second electrode disposed at a second side of the layer opposite to the first side, the first electrode and the second electrode electrically contacting the first contact area and the second contact area of the layer, respectively; wherein the first contact region and the second contact region of the dielectric structure include a first electrically conductive portion and a second electrically conductive portion, respectively, wherein the first electrically conductive portion and the second electrically conductive portion are electrically separated from the layer to adjust an electric characteristic of the two-dimensional material in the first contact area and in the second contact area of the layer by applying a voltage at the first electrically conductive portion and at the second electrically conductive portion, and wherein a device region is disposed between the first contact region and the second contact region of the dielectric structure corresponding to the device area of the layer, the device region including dielectric material.

According to various embodiments, the electronic device may further include: an electronic circuit (or any other circuit) electrically coupled to the first electrically conductive portion and the second electrically conductive portion, wherein the electronic circuit is configured to apply a voltage to the first electrically conductive portion and the second electrically conductive portion.

According to various embodiments, the device region disposed between the first contact region and the second contact region of the dielectric structure is free of electrically conductive material. According to various embodiments, the device region disposed between the first contact region and the second contact region of the dielectric structure includes a third electrically conductive portion that is electrically isolated from the first electrically conductive portion and the second electrically conductive portion by dielectric material.

According to various embodiments, the two-dimensional material includes graphene.

According to various embodiments, the first electrically conductive portion is electrically separated from the second electrically conductive portion, and an electronic circuit is configured to apply a first voltage to the first electrically conductive portion and a second voltage different from the first voltage to the second electrically conductive portion.

According to various embodiments, an electronic device may include: a layer including a two-dimensional material, a dielectric structure at a first side of the layer, wherein the dielectric structure includes at least one contact region defining at least one contact area of the layer and a device area of the layer adjacent to the at least one contact area of the layer; at least one electrode disposed at a second side of the layer opposite to the first side, wherein the at least one electrode is in direct physical contact with the at least one contact area of the layer; wherein the at least one contact region of the dielectric structure is configured to adjust an electric characteristic of the two-dimensional material in the at least one contact area of the layer so that the electric characteristic of the two-dimensional material in the at least one contact area of the layer is different from the electric characteristic of the two-dimensional material in the device area.

Further, the at least one contact region of the dielectric structure may include two directly neighboring contact regions that define two directly neighboring contact areas of the layer, wherein the device area of the layer extends between the two directly neighboring contact areas of the layer.

Further, the at least one contact region of the dielectric structure may be configured to generate an electrical field to adjust the electric characteristic of the two-dimensional material in the at least one contact area of the layer.

Further, the at least one contact region of the dielectric structure may include doped (e.g. permanently charged) dielectric material to provide the electrical field in the at least one contact area of the layer.

Further, the at least one contact region of the dielectric structure may include an electrically conductive portion that is electrically separated (e.g. by a dielectric layer) from the at least one contact area of the layer to provide the electrical field in the at least one contact area of the layer.

Further, the two-dimensional material may include or may be graphene.

Further, the layer may include a monolayer of the two-dimensional material. Further, the layer may include a graphene monolayer.

According to various embodiments, an electronic device may include: a layer including a two-dimensional material, a dielectric structure disposed at a first side of the layer, wherein the dielectric structure includes at least two contact regions defining at least two contact areas of the layer, wherein the at least two contact regions are spaced apart from each other so that a device area of the layer is provided between the at least two contact areas of the layer; at least two electrodes disposed at a second side of the layer opposite to the first side, the at least two electrodes electrically contacting the at least two contact areas of the layer; wherein each of the at least two contact regions of the dielectric structure includes a doped (e.g. permanently charged) dielectric material to adjust the electric characteristic of the two-dimensional material in the at least two contact areas of the layer, wherein a space between the at least two contact regions of the dielectric structure is free of the doped dielectric material.

Further, the at least two electrodes may be at least partially embedded in a dielectric layer, wherein the layer is disposed on the dielectric layer, and wherein the dielectric structure is disposed over the layer. The dielectric layer may be disposed on a semiconductor carrier.

Further, the dielectric structure may be disposed on a semiconductor carrier; wherein the space between the at least two contact regions of the dielectric structure may be filled with dielectric material, wherein the layer may be disposed over the dielectric structure, and wherein the at least two electrodes are disposed over the layer.

Further, the dielectric material that is disposed in the space between the at least two contact regions of the dielectric structure may include undoped dielectric material.

Further, the two-dimensional material may include or may be graphene.

According to various embodiments, an electronic device may include: a layer including a two-dimensional material, a dielectric structure disposed at a first side of the layer, wherein the dielectric structure includes at least two contact regions defining at least two contact areas of the layer, wherein the at least two contact regions are spaced apart from each other so that a device area of the layer is provided between the at least two contact areas of the layer; at least two electrodes disposed at a second side of the layer opposite to the first side, the at least two electrodes electrically contacting the at least two contact areas of the layer; wherein each of the at least two contact regions of the dielectric structure includes an electrically conductive portion that is electrically separated (e.g. by a dielectric layer) from the contact area of the layer to adjust the electric characteristic of the two-dimensional material in the at least two contact areas of the layer by applying a voltage at the electrically conductive portion.

According to various embodiments, the electronic device may further include: an electronic circuit electrically coupled to each of the electrically conductive portions, wherein the electronic circuit is configured to apply a voltage to each of the electrically conductive portions.

Further, the dielectric structure may be provided at least one of over or in a semiconductor carrier; wherein a space between the at least two contact regions of the dielectric structure is filled with dielectric material.

Further, the space between the at least two contact regions of the dielectric structure may be free of electrically conductive material.

Further, the two-dimensional material may include or may be graphene.

According to various embodiments, an electronic device may include: an electrically conductive layer including a first region and a second region, wherein the first region and the second region are electrically isolated from each other (e.g. by at least one trench filled with electrically insulating material or by a portion of electrically insulating material); a dielectric layer disposed over the electrically conductive layer; a layer including a two-dimensional material disposed over the dielectric layer, the layer including a first area disposed over the first region of the electrically conductive layer and a second area disposed over the second region of the electrically conductive layer; wherein the first region of the electrically conductive layer is electrically coupled to a first contact (pad) for applying a first electrical voltage to the first region (to provide a first electrical field in the first area of the layer) and wherein the second region of the electrically conductive layer is electrically coupled to a second contact pad for applying a second electrical voltage to the second region to provide a second electrical field in the second area of the layer (to provide different electric characteristics of the two-dimensional material in the first area and in the second area).

According to various embodiments, a method for operating an electronic device, wherein the electronic device includes: an electrically conductive layer including a first region and a second region, wherein the first region and the second region are electrically isolated from each other (e.g. by at least one trench filled with electrically insulating material or by a portion of electrically insulating material); a dielectric layer disposed over the electrically conductive layer; a layer including a two-dimensional material disposed over the dielectric layer, the layer including a first area disposed over the first region of the electrically conductive layer and a second area disposed over the second region of the electrically conductive layer; the method including: applying first voltage to the first region of the electrically conductive layer and applying a second voltage different from the first voltage to the second region of the electrically conductive layer (to provide different electric characteristics of the two-dimensional material in the first area and in the second area of the layer).

According to various embodiments, the first voltage may be in the range from about −100 V to about 100 V. According to various embodiments, the second voltage may be in the range from about −100 V to about 100 V.

According to various embodiments, an electronic device may include: a patterned electrically conductive layer including a first region and a second region adjacent to each other; a dielectric layer disposed over the patterned electrically conductive layer; a layer including a two-dimensional material disposed over the dielectric layer, the layer including a first area disposed over the first region of the electrically conductive layer and a second area disposed over the second region of the electrically conductive layer; wherein the dielectric layer has a first thickness between the first region of the patterned electrically conductive layer and the first area of the layer and a second thickness between the second region of the patterned electrically conductive layer and the second region of the layer, wherein the first thickness is different from the second thickness; wherein the electrically conductive layer is electrically coupled to a contact for applying an electrical voltage to the electrically conductive layer (e.g. to provide different electric characteristics of the two-dimensional material in the first area and in the second area.)

According to various embodiments, the first thickness may be in the range from about 3 nm to about 1 µm, e.g. in the range from about 10 nm to about 1 µm. According to various embodiments, the second thickness may be in the range from about 3 nm to about 1 µm, e.g. in the range from about 10 nm to about 1 µm.

According to various embodiments, a method may include: generating a first electrical field in a first area of a two-dimensional material layer to adapt a contact resistance between the first area of the two-dimensional material layer and an electrode that is in direct physical contact with the first area of the two-dimensional material layer; and generating a second electrical field that is different from the first electrical field in a second area of the two-dimensional material layer adjacent to the first area to adapt the electric characteristic of the two-dimensional material in the second area.

According to various embodiments, an electronic device may include: a dielectric structure and a layer disposed over the dielectric structure, the layer including a two-dimensional material, wherein the layer includes a contact region for electrically contacting the layer and a device region adjacent to the contact region; an electrode disposed at least one of over or in the dielectric structure for electrically contacting the contact area of the layer, wherein the dielectric structure is configured to change the electric characteristic of the two-dimensional material in the contact area of the layer so that the electric characteristic of the two-dimensional material in the contact area of the layer is different from the electric characteristic of the two-dimensional material in the device region.

According to various embodiments, the dielectric structure may include a dielectric material selected from a group of dielectric materials consisting of: an oxide; a nitride; and an oxynitride.

According to various embodiments, the dielectric structure may include a dielectric material selected from a group of dielectric materials consisting of: silicon oxide; silicon nitride; siliconoxynitride; silicon carbide; aluminum oxide; hafnium oxide, and zirconium oxide.

According to various embodiments, the two-dimensional material may include a metal chalcogenide.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. An electronic device, comprising:
    a layer comprising a two-dimensional material;
    a dielectric structure at a first side of the layer, wherein the dielectric structure comprises a first contact region and a second contact region, the first contact region defining a first contact area of the layer and the second contact region defining a second contact area of the layer, and the first contact region and the second contact region further defining a device area of the layer between the first contact area and the second contact area of the layer;
    a first electrode and a second electrode disposed at a second side of the layer opposite to the first side, wherein the first electrode is in direct physical contact with the first contact area of the layer and wherein the second electrode is in direct physical contact with the second contact area of the layer,
    wherein the first contact region and the second contact region of the dielectric structure are configured to adjust an electric characteristic of the two-dimensional material in the first contact area and in the second contact area of the layer, respectively, so that the electric characteristic of the two-dimensional material in the first contact area and in the second contact area of the layer is different from the electric characteristic of the two-dimensional material in the device area of the layer,
    wherein the first contact region and the second contact region of the dielectric structure are configured to generate an electrical field to adjust the electric characteristic of the two-dimensional material in the first contact area and in the second contact area of the layer, respectively, and wherein the first contact region and the second contact region of the dielectric structure each comprise doped dielectric material.

2. The electronic device of claim 1,
wherein the device area of the layer is free of further electrodes that are in direct physical contact with the layer.

3. The electronic device of claim 1,
wherein the first contact region and the second contact region of the dielectric structure are configured to provide the same electric characteristic of the two-dimensional material in the first contact area and in the second contact area of the layer.

4. The electronic device of claim 1,
wherein the first contact region and the second contact region of the dielectric structure are configured to provide different electric characteristics of the two-dimensional material in the first contact area and in the second contact area of the layer.

5. The electronic device of claim 1,
wherein the two-dimensional material comprises graphene.

6. The electronic device of claim 1,
wherein the layer comprises a monolayer of the two-dimensional material.

7. An electronic device, comprising:
a layer comprising a two-dimensional material,
a dielectric structure disposed at a first side of the layer, wherein the dielectric structure comprises a first contact region and a second contact region defining a first contact area and a second contact area of the layer, respectively, wherein the first contact region and the second contact region are spaced apart from each other so that a device area of the layer is provided between the first contact area and the second contact area of the layer;
a first electrode and a second electrode disposed at a second side of the layer opposite to the first side, the first electrode and the second electrode electrically contacting the first contact area and the second contact area of the layer, respectively;
wherein the first contact region and second contact region of the dielectric structure comprise a doped dielectric material to adjust an electric characteristic of the two-dimensional material in the first contact area and in the second contact area of the layer, respectively, wherein a space between the first contact region and the second contact region of the dielectric structure corresponding to the device area of the layer is free of the doped dielectric material.

8. The electronic device of claim 7,
wherein the first electrode and the second electrode are at least partially embedded in a dielectric layer, wherein the layer is disposed on the dielectric layer, and wherein the dielectric structure is disposed over the layer.

9. The electronic device of claim 8,
wherein the dielectric layer is disposed on a semiconductor carrier.

10. The electronic device of claim 7,
wherein the dielectric structure is disposed on a semiconductor carrier; wherein the space between the first contact region and the second contact region of the dielectric structure is filled with dielectric material, wherein the layer is disposed over the dielectric structure, and wherein the first electrode and the second electrode are disposed over the layer.

11. The electronic device of claim 10,
wherein the dielectric material disposed in the space between the first contact region and the second contact region of the dielectric structure comprises undoped dielectric material.

12. The electronic device of claim 7,
wherein the two-dimensional material comprises graphene.

13. An electronic device, comprising:
a layer comprising a two-dimensional material,
a dielectric structure disposed at a first side of the layer, wherein the dielectric structure comprises a first contact region and a second contact region defining a first contact area and a second contact area of the layer, respectively, wherein the first contact region and the second contact region are spaced apart from each other so that a device area of the layer is provided between the first contact area and the second contact area of the layer;
a first electrode and a second electrode disposed at a second side of the layer opposite to the first side, the first electrode and the second electrode electrically contacting the first contact area and the second contact area of the layer, respectively;
wherein the first contact region and the second contact region of the dielectric structure comprise a first electrically conductive portion and a second electrically conductive portion, respectively, wherein the first electrically conductive portion and the second electrically conductive portion are electrically separated from the layer to adjust an electric characteristic of the two-dimensional material in the first contact area and in the second contact area of the layer by applying a voltage at the first electrically conductive portion and at the second electrically conductive portion, and wherein a device region is disposed between the first contact region and the second contact region of the dielectric structure corresponding to the device area of the layer, the device region comprising dielectric material.

14. The electronic device of claim 13, further comprising:
an electronic circuit electrically coupled to the first electrically conductive portion and the second electrically conductive portion, wherein the electronic circuit is configured to apply a voltage to the first electrically conductive portion and the second electrically conductive portion.

15. The electronic device of claim 13,
wherein the device region disposed between the first contact region and the second contact region of the dielectric structure is free of electrically conductive material.

16. The electronic device of claim 13,
wherein the two-dimensional material comprises graphene.

17. The electronic device of claim 13,
wherein the first electrically conductive portion is electrically separated from the second electrically conductive portion, and wherein an electronic circuit is configured to apply a first voltage to the first electrically conductive portion and a second voltage different from the first voltage to the second electrically conductive portion.

18. An electronic device, comprising:
a layer comprising a two-dimensional material;
a dielectric structure at a first side of the layer, wherein the dielectric structure comprises a first contact region and a second contact region, the first contact region defining a first contact area of the layer and the second contact region defining a second contact area of the layer, and the first contact region and the second contact region further defining a device area of the layer between the first contact area and the second contact area of the layer;

a first electrode and a second electrode disposed at a second side of the layer opposite to the first side, wherein the first electrode is in direct physical contact with the first contact area of the layer and wherein the second electrode is in direct physical contact with the second contact area of the layer, wherein the first contact region and the second contact region of the dielectric structure are configured to adjust an electric characteristic of the two-dimensional material in the first contact area and in the second contact area of the layer, respectively, so that the electric characteristic of the two-dimensional material in the first contact area and in the second contact area of the layer is different from the electric characteristic of the two-dimensional material in the device area of the layer, wherein the first contact region and the second contact region of the dielectric structure are configured to generate an electrical field to adjust the electric characteristic of the two-dimensional material in the first contact area and in the second contact area of the layer, respectively, and wherein the first contact region comprises a first electrically conductive portion and wherein the second contact region of the dielectric structure comprises a second electrically conductive portion, wherein the first electrically conductive portion and the second electrically conductive portion are electrically separated from the layer.

* * * * *